(12) United States Patent
Yagi et al.

(10) Patent No.: US 7,994,481 B2
(45) Date of Patent: Aug. 9, 2011

(54) RADIATION IMAGING APPARATUS, METHOD OF CONTROLLING THE SAME, AND RADIATION IMAGING SYSTEM

(75) Inventors: Tomoyuki Yagi, Honjo (JP); Hitoshi Inoue, Yokohama (JP); Hideto Shiozawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 60 days.

(21) Appl. No.: 12/023,539

(22) Filed: Jan. 31, 2008

(65) Prior Publication Data
US 2009/0001276 A1    Jan. 1, 2009

(30) Foreign Application Priority Data

Feb. 1, 2007 (JP) .................................. 2007-023385
Jan. 23, 2008 (JP) .................................. 2008-012950

(51) Int. Cl.
G01T 1/20    (2006.01)
G01T 1/00    (2006.01)

(52) U.S. Cl. ......... 250/370.09; 250/390.11; 250/370.11; 250/370.08; 250/363.09; 348/E5.086; 378/116; 378/98.9; 378/114

(58) Field of Classification Search ............... 378/98.12, 378/114, 116, 98.9; 250/363.09, 390.11, 250/370.11, 580, 208.1, 370.08, 363.07, 250/370.09; 348/E5.086
See application file for complete search history.

(56) References Cited

U.S. PATENT DOCUMENTS

| | | | |
|---|---|---|---|
| 4,945,552 A | 7/1990 | Ueda et al. | 378/98.11 |
| 5,224,141 A | 6/1993 | Yassa et al. | 378/98.2 |
| 6,453,008 B1 | 9/2002 | Sakaguchi et al. | 378/98.7 |
| 7,142,705 B2 | 11/2006 | Inoue et al. | 382/132 |
| 7,158,661 B2 | 1/2007 | Inoue | 382/128 |
| 7,196,725 B1 | 3/2007 | Saigusa et al. | 348/245 |
| 7,221,735 B2 | 5/2007 | Inoue | 378/97 |
| 7,227,926 B2 | 6/2007 | Kameshima et al. | 378/98.9 |
| 7,342,221 B2 | 3/2008 | Takenaka et al. | 250/252.1 |
| 7,343,000 B2 | 3/2008 | Kameshima et al. | 378/98.9 |
| 7,512,214 B2 * | 3/2009 | Takenaka et al. | 378/98.12 |
| 2003/0185342 A1 | 10/2003 | Petrick | 378/98.9 |
| 2003/0223629 A1 | 12/2003 | Inoue | 382/132 |
| 2004/0096036 A1 | 5/2004 | Yanoff et al. | 378/98.9 |
| 2005/0151086 A1 | 7/2005 | Spahn | 250/370.08 |
| 2005/0199834 A1 | 9/2005 | Takenaka et al. | 250/580 |

(Continued)

FOREIGN PATENT DOCUMENTS

FR    2788360    7/2000

(Continued)

*Primary Examiner* — David Porta
*Assistant Examiner* — Yara Green
(74) *Attorney, Agent, or Firm* — Fitzpatrick, Cella, Harper & Scinto

(57) ABSTRACT

There are provided an apparatus capable of complying with arbitrary data acquisition period (frame rate) change instruction without increasing load and cost, and a method and a system for controlling such an apparatus. To realize this, in the present invention, there are included an area sensor for reading out an electric signal accumulated in a plurality of pixels arranged in a matrix, line by line, and a control unit for controlling the area sensor. The area sensor operates in a first operation for deriving radiation image data by reading during irradiation with radiation, and a second operation for deriving the radiation image data by reading during non-irradiation with radiation, alternately. The control unit switches a period for deriving the radiation image data during a time period from an end of the reading in the first operation until an end of the reading in the second operation.

24 Claims, 13 Drawing Sheets

U.S. PATENT DOCUMENTS

| | | |
|---|---|---|
| 2005/0200720 A1 | 9/2005 | Kameshima et al. ...... 348/220.1 |
| 2005/0220269 A1 | 10/2005 | Endo et al. .................... 378/114 |
| 2005/0264665 A1 | 12/2005 | Endo et al. .................... 348/294 |
| 2006/0188061 A1 | 8/2006 | Takenaka et al. ................ 378/62 |
| 2006/0192130 A1 | 8/2006 | Yagi ........................ 250/370.14 |
| 2006/0289774 A1 | 12/2006 | Endo et al. ............... 250/370.09 |
| 2007/0019847 A1 | 1/2007 | Inoue et al. .................... 382/128 |
| 2007/0040099 A1 | 2/2007 | Yokoyama et al. ........ 250/208.1 |
| 2007/0080299 A1 | 4/2007 | Endo et al. ............... 250/370.09 |
| 2007/0096032 A1 | 5/2007 | Yagi et al. ................ 250/370.11 |
| 2007/0125952 A1 | 6/2007 | Endo et al. .................... 250/369 |
| 2007/0131843 A1 | 6/2007 | Yokoyama et al. ........... 250/205 |
| 2007/0210258 A1 | 9/2007 | Endo et al. ............... 250/370.09 |
| 2007/0290143 A1 | 12/2007 | Kameshima et al. .... 250/370.09 |
| 2007/0291904 A1 | 12/2007 | Takenaka et al. ............. 378/207 |
| 2007/0297567 A1 | 12/2007 | Takenaka et al. ............ 378/98.2 |
| 2008/0011958 A1 | 1/2008 | Endo et al. ............... 250/370.08 |
| 2008/0013686 A1 | 1/2008 | Kameshima et al. ........... 378/98 |
| 2008/0029688 A1 | 2/2008 | Yagi et al. .................. 250/208.1 |
| 2008/0054182 A1 | 3/2008 | Yokoyama et al. ...... 250/370.09 |
| 2008/0083876 A1 | 4/2008 | Endo et al. .................... 250/369 |
| 2008/0151070 A1 | 6/2008 | Shiozawa et al. .......... 348/222.1 |
| 2008/0217548 A1 | 9/2008 | Kameshima et al. .... 250/370.09 |
| 2008/0226031 A1 | 9/2008 | Yokoyama et al. .......... 378/98.7 |

FOREIGN PATENT DOCUMENTS

JP        2004-194702        7/2004

* cited by examiner

PIN TYPE PHOTOELECTRIC
CONVERSION ELEMENT

MIS TYPE PHOTOELECTRIC
CONVERSION ELEMENT

DIRECT TYPE PHOTOELECTRIC
CONVERSION ELEMENT

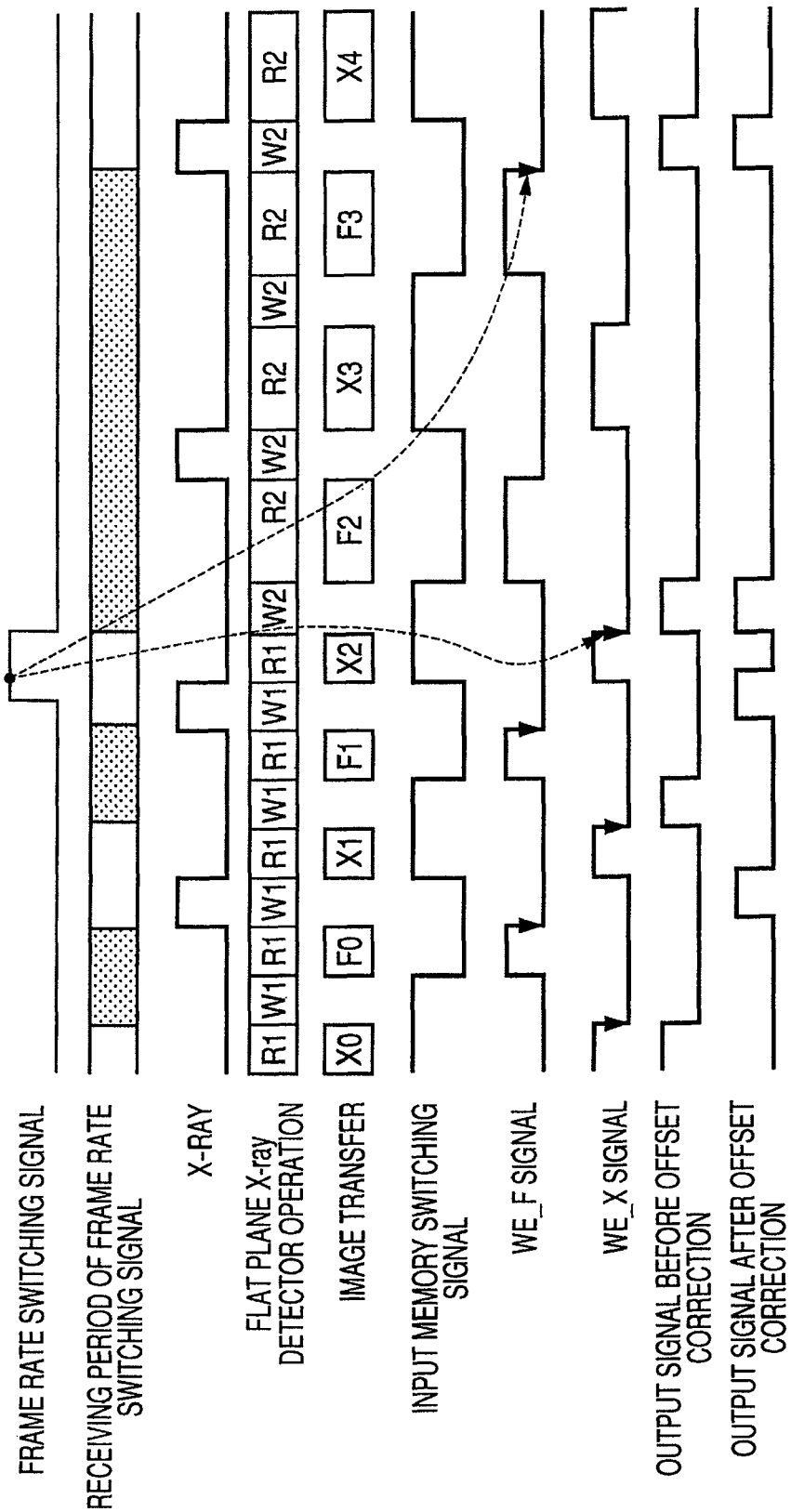

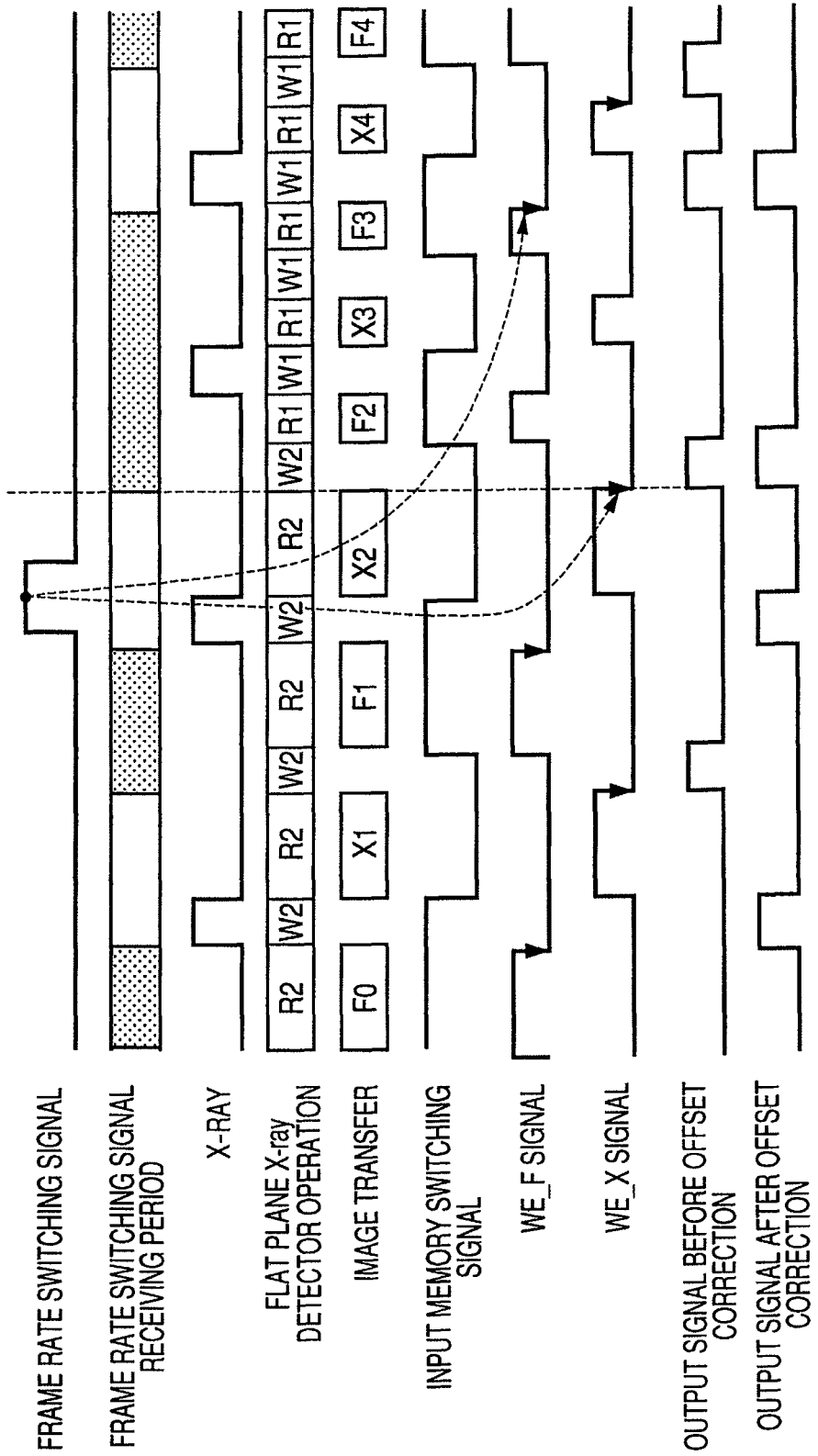

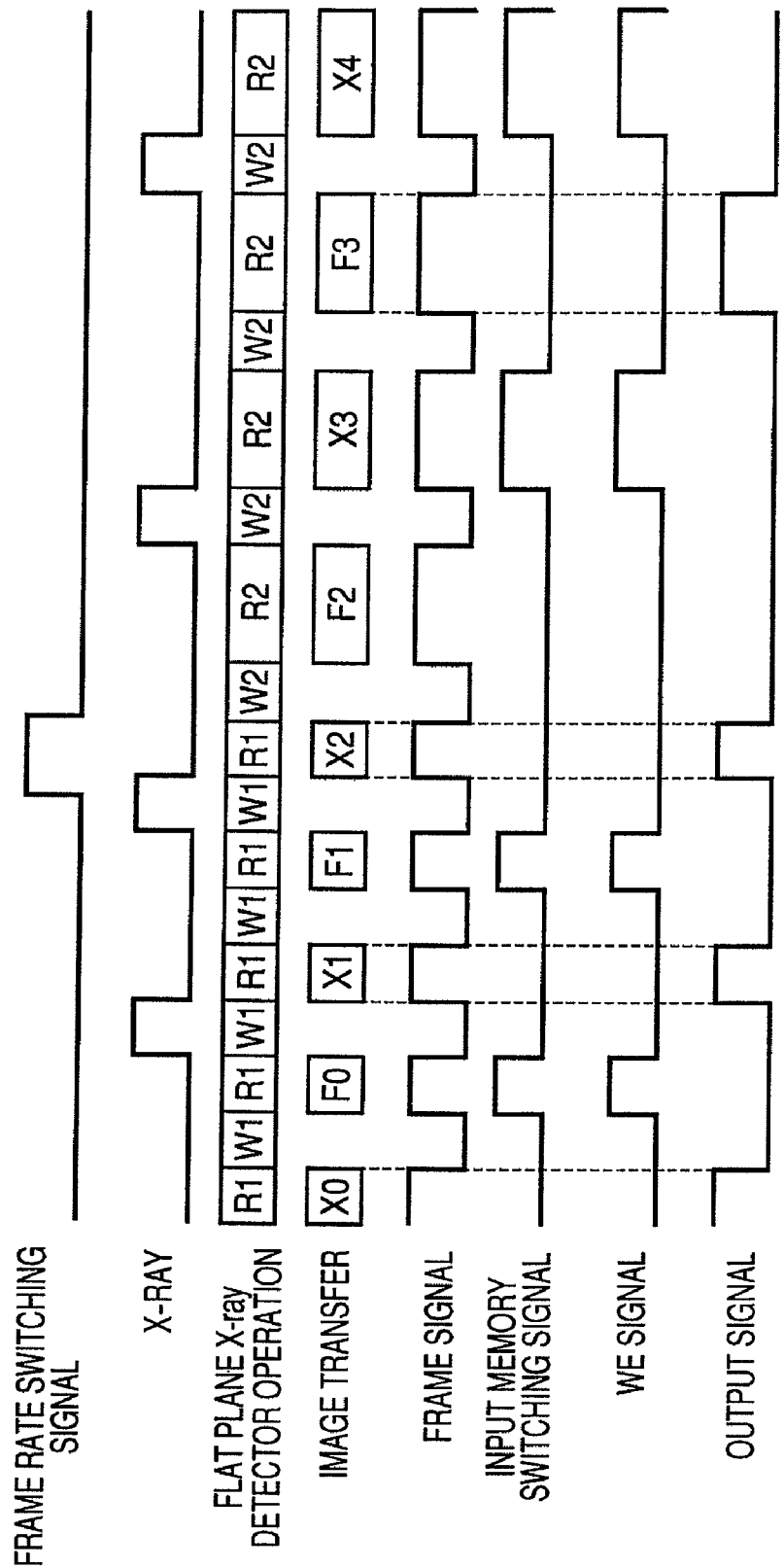

C-ARM (TYPE OF RUNNING ON CEILING)

C-ARM (MOBILE TYPE)

RADIATION IMAGING APPARATUS, METHOD OF CONTROLLING THE SAME, AND RADIATION IMAGING SYSTEM

BACKGROUND OF THE INVENTION

1. Field of the Invention

The present invention relates to a radiation imaging apparatus, a method of controlling such a radiation imaging apparatus, and a radiation imaging system.

2. Description of the Related Art

In recent years, with development of the semiconductor technology, there are put into practice and are popularized digital X-ray imaging apparatuses using a two-dimensionally arranged sensor in which conversion elements for converting light into an electric signal are formed on a glass substrate.

In U.S. Pat. No. 6,453,008, there is described a radiation detector including plural offset memories having offset data which have been acquired in advance in correspondence with plural modes (sequential read-out, pixel addition, trimming, high frame rate and high irradiation), and which selectively uses an appropriate one of the offset memories in accordance with the corresponding mode.

Moreover, in Japanese Patent Application Laid-Open No. 2004-194702, there is described a digital radiation imaging apparatus adapted for collecting offset data in which a change of scanning mode (fluoroscopy, photography) is performed in advance.

In fluoroscopy (moving picture radiographing), the frame rate, i.e., the interval between a series of operations for irradiating an object with X-rays to acquire radiation image data is switched for three reasons, described below.

As the first reason, there is mentioned a desired reduction in dosage of exposure to radiation. In recent years, where there is high interest relating to X-ray exposure, and an X-ray diagnosis apparatus or a radiographing technique which can perform radiographing with as low a dosage of exposure to radiation as possible is required, there has been employed an approach to reduce the dosage of exposure to radiation as low as possible by pulse fluoroscopy and setting of a fluoroscopic frame rate. Pulse fluoroscopy is a fluoroscopic radiographing method of irradiating the object with X-rays in a pulse form in correspondence with a set frame rate. The frame rate which has been set in this pulse fluoroscopy is simply X-ray irradiation quantity per unit time. In the case of pulse fluoroscopy, a worker can perform radiographing with the frame rate lowered to a level such that there is no inconvenience in operation, while lowering the dosage of exposure to radiation of the patient. For example, there is mentioned an example where, in a series of works of acquisition of mask image, contrast medium injection start by injector and contrast medium injection end in angiography, frame rate is suitably switched in accordance with working state to suppress dosage of exposure to radiation of a patient as low as possible. Thus, there is required a fluoroscopic system capable of arbitrarily switching frame rate.

The second reason is synchronization with movement of an object. Applications to perform radiographing in synchronism with various movements of the object such as heartbeat or movement of a patient's bed have been studied and developed.

The third reason is that the fluoroscopic system is being applied to various X-ray diagnosis systems. One application is simple CT-like application. CT (Computed Tomography) is a technique for circumferentially scanning the periphery of an object by X-rays to obtain an X-ray tomographic image of an object. Recently, CT has been added, as an optional function of a fluoroscopic system using a flat plane X-ray detector as a detector. In the fluoroscopic system, since an X-ray source and a detector are oppositely disposed, rotation is performed around an object so that radiographing similar to CT can be performed. Since synchronization between angular velocity of rotation and radiographing frame is essential in order to obtain a precise CT image, it is necessary to acquire an image by taking change of angular velocity from start of movement into consideration. For this reason, it is required to be able to make arbitrary changes in frame rate.

As described above, there is the problem that while there is a requirement of switching the frame rate in the fluoroscopic system, offset correction is not sufficient immediately after switching of frame rate in the flat plane X-ray detector as mentioned in the previously cited patent documents. Offset correction is to correct an output which is not dependent upon X-ray quantity which is output from the flat plane X-ray detector. As element of offset, there are various elements; there are electric offset of a read-out circuit and an offset based on dark current which is output from conversion element. The reason why offset correction cannot be sufficiently performed after frame rate switching is that storage time varies depending upon the frame rate. Further, as an element for increasing such an error, there are mentioned gain setting switching of a read-out circuit in conformity with switching of frame rate, and change of the number of lines acquired by pixel addition.

In patent documents 1 and 2 cited above, there is employed an approach to have offset correction data for every switching pattern of frame rate to deal with such problems.

SUMMARY OF THE INVENTION

However, with this method, in order to accommodate a large number of frame rates, it is necessary to have a great quantity of offset correction data. It is required to provide a memory apparatus capacity therefor and a system for analyzing switching of frame rate. Further, offset itself is not always constant. Since offset changes depending upon use environment and the number of working years of an apparatus, and X-ray quantity at the time of performing radiographing, etc., updating and management of preserved offset data are required. From this it will be understood that the system is complicated and becomes expensive.

An object of the present invention is to provide a radiation imaging apparatus, a method of controlling the same, and a radiation imaging system which can deal with an arbitrary data acquisition period (frame rate) change instruction without increasing load and cost.

A radiation imaging apparatus according to the present invention is directed to a radiation imaging apparatus including: an area sensor for reading out an electric signal accumulated in a plurality of pixels arranged in a matrix, a line by line; and a control unit for controlling the area sensor, wherein the area sensor operates in a first operation for deriving a radiation image data by the reading under an irradiation with a radiation, and a second operation for deriving the radiation image data by the reading under a non-irradiation with the radiation, alternately; and the control unit switches a period for deriving the radiation image data during a time period from an end of the reading in the first operation until an end of the reading in the second operation.

Moreover, a radiation imaging apparatus according to the present invention is directed to a radiation imaging apparatus including: an area sensor for reading out an electric signal accumulated in a plurality of pixels arranged in a matrix, a line by line, to derive a two-dimensional data; and a control unit for controlling the area sensor, wherein the area sensor operates in a first operation for deriving a radiation image data by the reading under an irradiation with a radiation, and a second operation for deriving the radiation image data by the reading under a non-irradiation with the radiation, alternately; and the control unit switches a period for deriving two dimensional data from a first period of the first operation into a second period different from the first period for a time period, during a time period of the second operation.

Further, a method of controlling a radiation imaging apparatus according to the present invention is directed to a method of controlling a radiation imaging apparatus including an area sensor for reading out an electric signal accumulated in a plurality of pixels arranged in a matrix, a line by line, wherein the area sensor operates in a first operation for deriving a radiation image data by the reading under an irradiation with a radiation, and a second operation for deriving the radiation image data by the reading under a non-irradiation with the radiation, alternately; and the method includes the step of controlling the area sensor, to switch a period for deriving the radiation image data during a time period from an end of the reading in the first operation until an end of the reading in the second operation.

Furthermore, a method of controlling a radiation imaging apparatus according to the present invention is directed to a method of controlling a radiation imaging apparatus including an area sensor for reading out an electric signal accumulated in a plurality of pixels arranged in a matrix, a line by line, to derive two-dimensional data, wherein the area sensor operates in a first operation for deriving a radiation image data by the reading under an irradiation with a radiation, and a second operation for deriving the radiation image data by the reading under a non-irradiation with the radiation, alternately; and the method includes a step of controlling the area sensor to switch a period for deriving the two-dimensional data from a first period of the first operation into a second period different from the first period, during the time period of the second operation.

In accordance with the present invention, since it is unnecessary to store offset correction data every switching pattern of frame rate, offset correction can be made by a simple and low-cost configuration.

Further features of the present invention will become apparent from the following description of exemplary embodiments with reference to the attached drawings.

BRIEF DESCRIPTION OF THE DRAWINGS

FIGS. 5A and 5B are diagrams illustrating an example of the configuration of offset correction unit and a processing method thereof.

FIG. 6 is a diagram illustrating a processing method by offset correction unit in the case where switching is performed in a direction where frame rate is increased.

FIGS. 8A and 8B are diagrams illustrating a configuration example of offset correction unit 602 according to a second exemplary embodiment of the present invention, and a processing method thereof.

DESCRIPTION OF THE EMBODIMENTS

First Exemplary Embodiment

Figure 2:
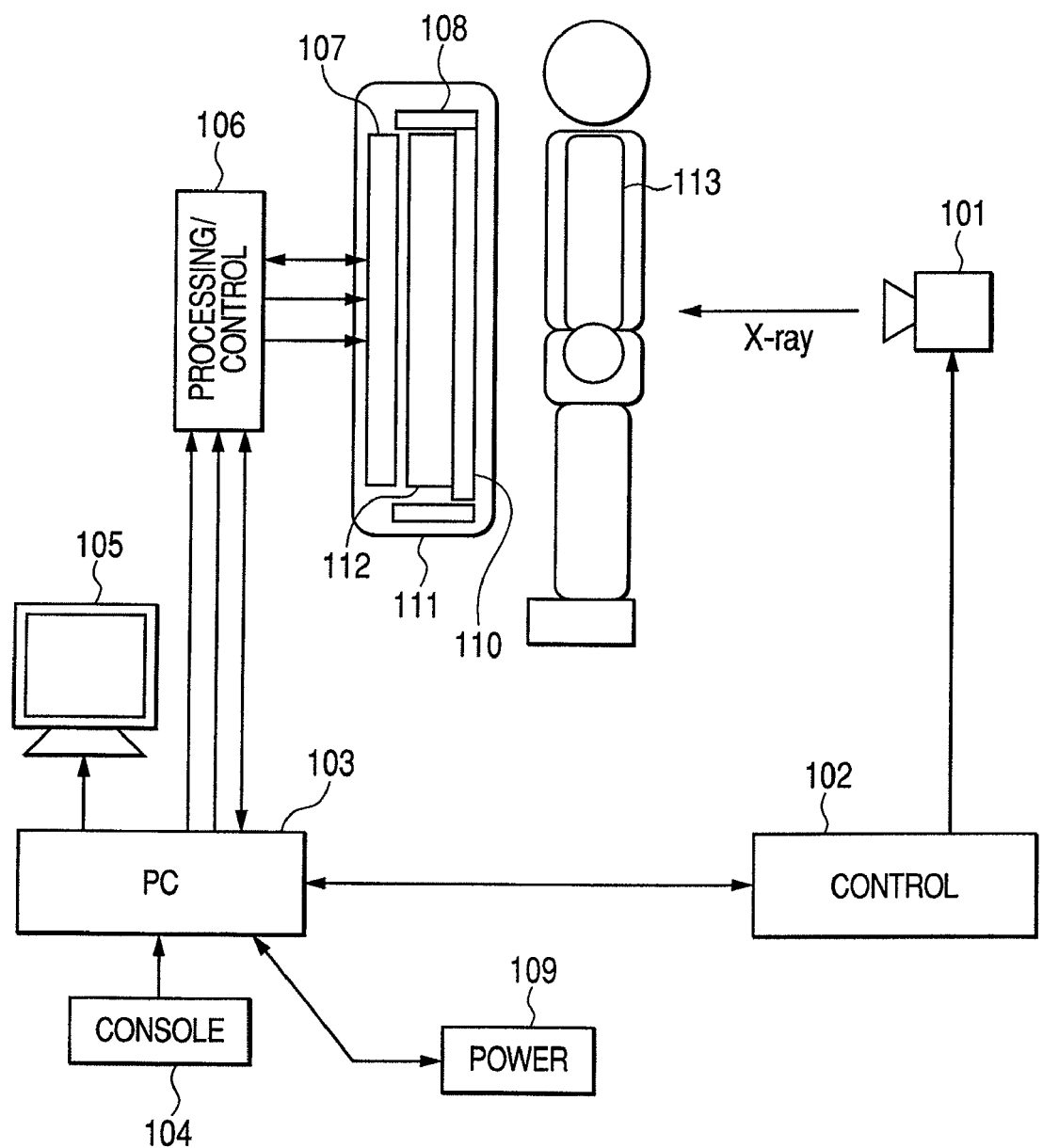
FIG. 2 is a diagram illustrating an example of the configuration of a digital radiation (X-ray) imaging system according to the first exemplary embodiment of the present invention.

FIG. 2 is a diagram illustrating an example of the configuration of a digital radiation (X-ray) imaging system according to a first exemplary embodiment of the present invention. This digital radiation imaging system includes an X-ray source 101, an X-ray controller 102, and a digital radiation imaging apparatus. The X-ray source 101 is a radiation generator for generating and irradiating radioactive rays (hereinafter simply referred to as radiation as occasion may demand) (X-rays). The digital radiation imaging apparatus includes a control PC (Personal Computer) 103, a control console 104, a monitor 105, an image processing and control circuit 106, a power supply unit 109, and a flat plane X-ray detector 111. Specifically, the flat plane X-ray detector 111 is a two-dimensional area sensor including a system circuit 107, a read-out circuit 108, a sensor array 110 and a vertical drive circuit 112; and serves to convert radiation into an electric signal to output two-dimensional data. A part designated at reference numeral 113 is an object.

The control PC 103 is connected to the power supply unit 109, and serves to control the X-ray controller 102 and the image processing and control circuit 106 in accordance with an operation of the control console 104 by user to display image and data on the monitor 105. The X-ray source 101 irradiates X-rays toward the object (human being) 113 in accordance with control of the X-ray controller 102. The sensor array 110 includes two-dimensionally arranged conversion elements for converting X-rays transmitted through the object 113 and bearing information of the object 113 into an electric signal to accumulate the electric signal. The vertical drive circuit 112 controls switching elements of the sensor array 110 to read out, line by line, image signals. The read-out circuit 108 reads out an image signal of the sensor array 110 to amplify the image signal. The system circuit 107 converts the image signal from analog into a digital signal. The image processing and control circuit 106 serves to implement image processing to the image signal which has been read out through the system circuit 107. The control PC 103 can display, on the monitor 105, an image which has been processed at the image processing and control circuit 106.

Moreover, the control PC 103 can output a control signal for driving the sensor array 110 to the read-out circuit 108 and the vertical drive circuit 112, take synchronization with the X-ray source 101, and perform image processing or storage•display of image. Moreover, the system circuit 107 includes a regulator or an operation timing circuit for creating a voltage necessary at signal amplifier circuits within the sensor array 110, the vertical drive circuit 112 and the read-out circuit 108.

Figure 3:
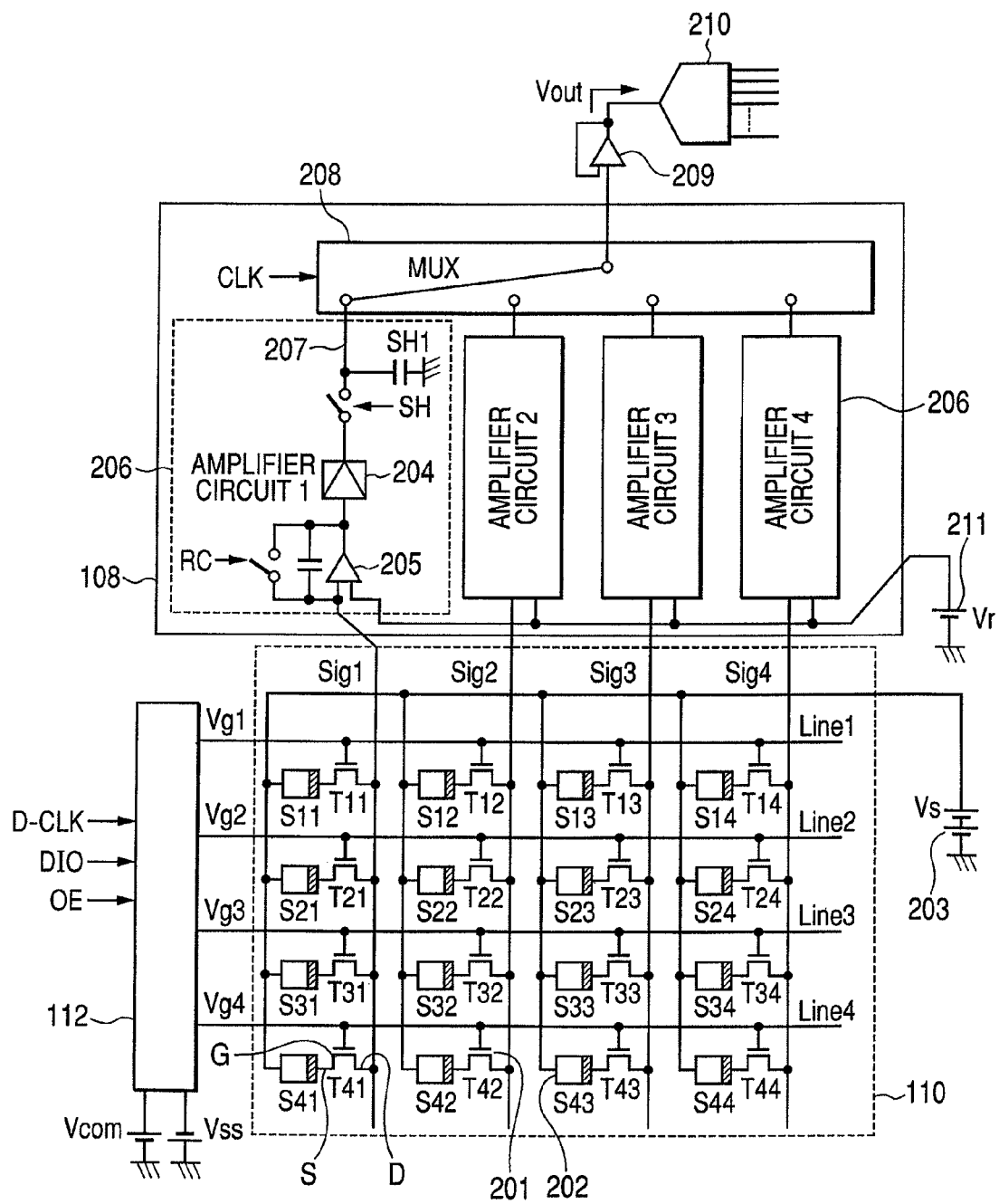
FIG. 3 is a diagram illustrating an example of the configuration of a flat plane X-ray detector.

FIG. 3 is a diagram illustrating an example of the configuration of the flat plane X-ray detector 111. This flat plane X-ray detector 111 includes TFTs (Thin Film Transistors) 201, conversion elements 202, a sensor power source 203, a variable gain amplifier 204, an integration amplifier 205, an amplifier circuit 206, a sampling and holding circuit 207, a multiplexer 208, a buffer amplifier 209, a A/D converter 210, and an amplifier reference power source 211. The TFT 201 has gate G, source S and drain D.

The sensor array 110 is adapted so that there are two-dimensionally arranged pixels in which conversion elements 202 for converting radiation into an electric signal and TFTs (switching elements) 201 for outputting electric signals which have been converted by the conversion elements 202 are combined.

While flat plane X-ray detector 111 having 4×4 pixels will be described here for the brevity of description, the number of pixels of the flat plane X-ray detector used in an actual radiation imaging apparatus is 1000×1000 to 2800×2800.

The sensor array 110 is adapted so that there are two-dimensionally arranged pixels in which conversion elements 202 and TFTs 201 serving as switching elements are combined. Moreover, signal wires Sig 1 to Sig 4 for transferring charges accumulated in the conversion elements 202, drive wires Vg1 to Vg4 connected to the gates G of the TFTs 201, and respective common wires of line for supplying a voltage Vs necessary for the conversion element 202 are connected to the sensor array 110. The read-out circuit 108 is connected to signal wires Sig 1 to Sig 4 of the sensor array 110, and the vertical drive circuit 112 is connected to the drive wires Vg1 to Vg4 thereof.

The first Line 1 includes pixels of conversion elements S11, S12, S13 and S14 controlled through the drive wire Vg1. The second Line 2 includes pixels of conversion elements S21, S22, S23 and S24 controlled through the drive wire Vg 2. The third Line 3 includes pixels of conversion elements S31, S32, S33 and S34 controlled through the drive wire Vg 3. The fourth Line 4 includes pixels of conversion elements S41, S42, S43 and S44 controlled through the drive wire Vg 4.

The read-out circuit 108 is connected to respective signal wires Sig 1 to Sig 4, and includes, therewithin, four amplifier circuits 206 which are one-to-one connected to signal wires Sig 1 to Sig 4. The amplifier circuit 206 includes integration amplifier 205 for accumulating and amplifying charges which have been transferred from the conversion element 202, variable gain amplifier 204 for amplifying a signal of the integration amplifier 205, and sampling and holding circuit 207 for temporarily holding an output from the variable gain amplifier 204. The amplifier circuit 206 performs amplification and sampling of a signal. The integration amplifier 205 is adapted to change the number of capacitors connected to the feedback part of the amplifier thereby to have the ability to change amplification factor.

At the succeeding stage of the sampling and holding circuit 207 within the amplifier circuit 206, there is provided multiplexer 208 for reading out, in a time series manner, an electric signal which has been accumulated in the sampling and holding circuit 207. The multiplexer 208 sequentially transfers electric signals (image signals) to the buffer amplifier 209. The buffer amplifier 209 amplifies an image signal to output an image signal $V_{OUT}$ to A/D converter 210. The A/D converter 210 converts an analog signal which is output from the buffer amplifier 209 into a digital signal.

The sensor power source 203 is a power source for supplying a voltage Vs required for allowing the conversion element 202 to convert radioactive rays or rays of light into charges. Respective conversion elements 202 are supplied with voltage Vs from the sensor power source 203 through a shared line. Moreover, magnitude or polarity of voltage value used and the number of power supplies are changed depending upon the structure or the conversion method of the conversion element 202. Those factors are selected so that the conversion element 202 can obtain sufficient S/N.

The TFTs 201 of the sensor array 110 are connected in a form such that the TFTs 201 in a lateral direction and drive wires Vg 1 to Vg 4 are shared, and the vertical drive circuit 112 is connected to drive wires Vg 1 to Vg 4. The vertical drive circuit 112 outputs drive signals including voltages Vcom and Vss, which are input, of the two power sources in accordance with pulses D-CLK, OE and DIO which are input from the control circuit 106. Further, the vertical drive circuit 112 can sequentially output drive signals to drive wires Vg 1 to Vg 4 connected thereto. By the operation of this vertical drive circuit 112, ON/OFF of the TFTs 201 of one line in a lateral direction can be controlled.

As conversion element 202 used for pixels of the above-described sensor array 110, there may be used an MIS-type (Metal-Insulator-Semiconductor) conversion element, a PIN-type conversion element, and a direct-type conversion element.

Figure 4A:
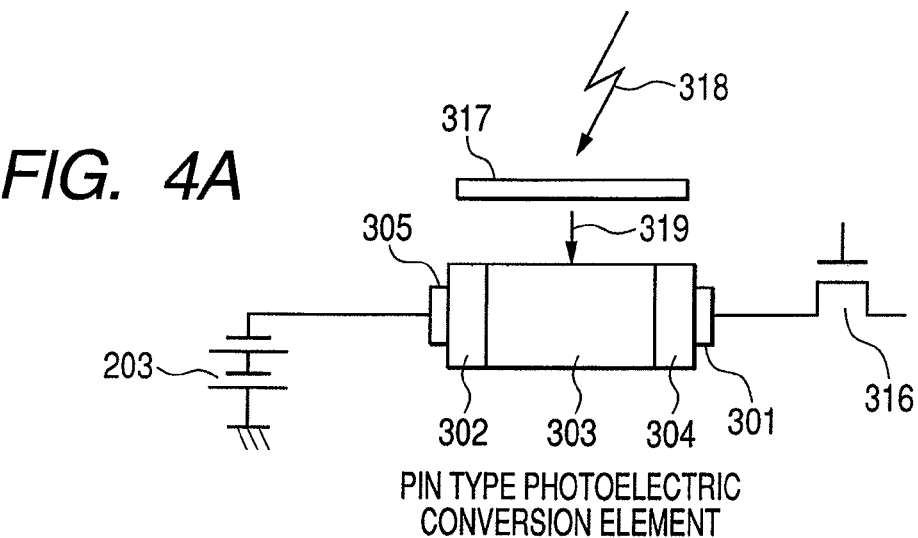
FIGS. 4A, 4B and 4C are diagrams illustrating an example of the structure of a conversion element.
Figure 4B:
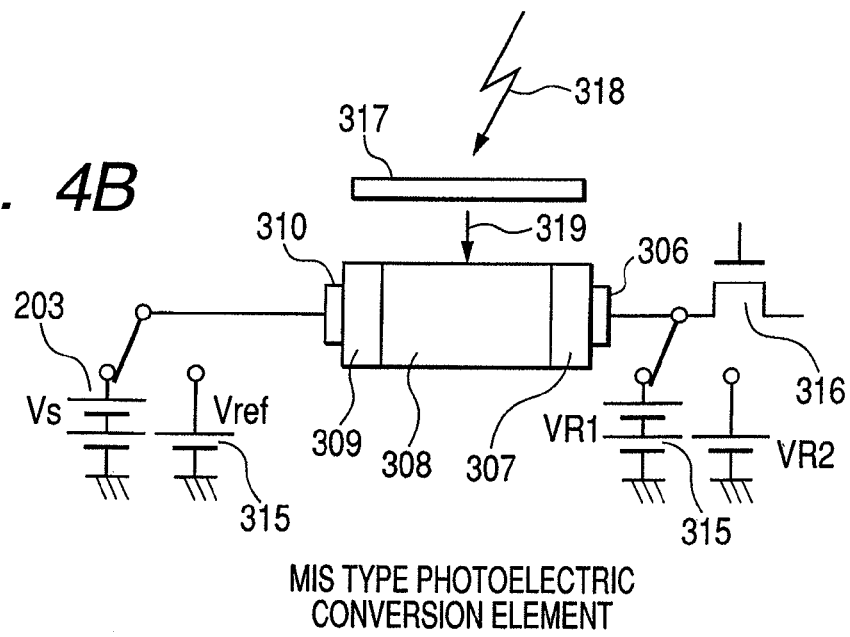
Figure 4C:
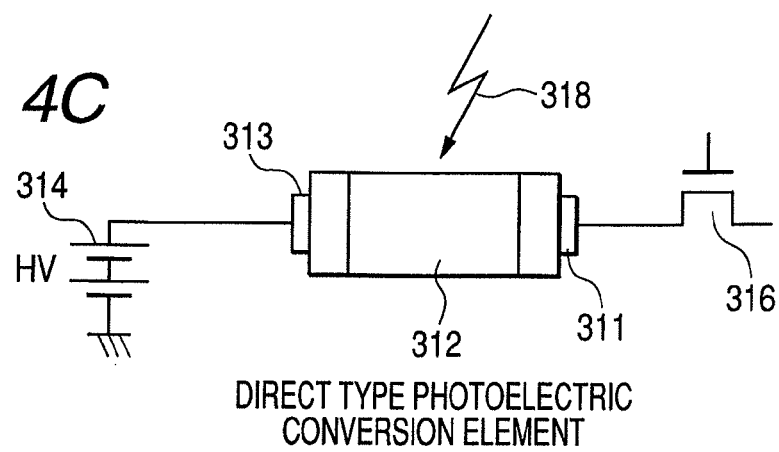

FIGS. 4A to 4C are diagrams illustrating an example of the structure of conversion element 202. FIG. 4A illustrates an example of the structure of PIN type conversion element. The conversion element 202 includes a PIN lower electrode 301, a P-layer 302, an I-layer 303, an N-layer 304 and a PIN upper electrode 305. The circuit component designated at reference numeral 203 indicates sensor power source. The circuit component designated at reference numeral 316 is a TFT. In addition, the part designated at reference numeral 317 is a phosphor (a wavelength-converting body). Designated at reference numeral 318 are X-rays (or radioactive rays), and at reference 319, visible rays. The PIN-type conversion element is such that the phosphor 317 for converting X-rays 318 into visible rays and the PIN photodiode are combined. The PIN photodiode is configured so as to include P layer (P-type impurity semiconductor layer) 302 containing P-type amorphous silicon, an I layer (intrinsic semiconductor layer) 303 containing intrinsic amorphous silicon, and an N layer (N-type impurity semiconductor layer) 304 containing N-type amorphous silicon. In the conversion element as described above, X-rays 318 that have been transmitted through the human body and bearing information of the human body are converted into visible rays 319 by the phosphor 317. These visible rays 319 are converted into charges by the PIN photodiode. The charges thus produced are accumulated at parasitic capacitance between the TFT 316 and the PIN photodiode.

FIG. 4B illustrates an example of the structure of the MIS-type conversion element. This MIS type conversion element includes an MIS lower electrode 306, an insulating layer 307, an a-Si layer (intrinsic semiconductor layer) 308, an N⁺ layer (N-type impurity semiconductor layer) 309, and an MIS upper electrode 310. The circuit component designated at reference numeral 203 is a sensor power source. The circuit component designated at reference numeral 315 indicates a refreshing power source. The circuit component designated at reference numeral 316 is a TFT. The part designated at reference numeral 317 is a phosphor. Reference numeral 318 indicates X-rays, and 319, visible rays. The MIS-type conversion element is such that phosphor 317 for converting X-rays 318 into visible rays 319 and the MIS-type photosensor are combined. The MIS-type photosensor is configured so as to include an N⁺ layer 309 containing N⁺ type amorphous silicon, an a-Si layer 308 containing intrinsic amorphous silicon, and an insulating layer 307 containing amorphous nitride silicon film. In the MIS-type conversion element as described above, X-rays 318 that have been transmitted through the human body and bearing information of the human body are converted into visible rays 319 by phosphor 317, and the visible rays 319 thus obtained are converted into charges by the MIS-type photosensor. The charges thus produced are accumulated between a-Si layer 308 and insulating layer 307. Since charges which have been produced once are continued to be accumulated in the MIS-type conversion element, it is necessary to perform a refreshing operation to sweep out, periodically or after accumulation of a determined quantity of charges, those charges which have been accumulated in the a-Si layer 308 and the insulating layer 307. In the MIS-type conversion element for performing this refreshing operation, it is required to have two or more voltage values of sensor bias.

Since the PIN-type conversion element and the MIS-type conversion element which have been previously described convert X-rays 318 into visible rays 319 by using phosphor 317 to further convert the visible rays 319 into an electric signal, those conversion elements are called indirect-type conversion elements. The indirect type conversion element is configured so as to include a photoelectric conversion element such as a PIN photodiode or MIS photosensor, and wavelength converting body for converting X-rays 318 into visible rays 319. In the PIN-type conversion element of FIG. 4A and the MIS-type conversion element of element of FIG. 4B, phosphor (wavelength converting body) 317 is caused to be closely in contact with the light-incident surface side of the photoelectric conversion element. The phosphor 317 performs wavelength conversion of X-rays 318 to generate visible rays 319.

FIG. 4C illustrates an example of the structure of the direct-type conversion element. This direct-type conversion element includes a pixel electrode 311, an a-Se layer 312, and a sensor bias electrode 313. The circuit component designated at reference numeral 314 is an HV power supply. The circuit component designated at reference numeral 316 is a TFT. Reference numeral 318 indicates X-rays. The direct-type conversion element uses a material to directly convert X-rays 318 into an electric signal. As a material, an amorphous selenium layer 312 may be used. When a voltage of several kV is applied, this amorphous selenium can convert X-rays 318 into charges.

The TFT, the MIS-type conversion element and the PIN-type conversion element which have been described above are fabricated by amorphous silicon process. The reason why the amorphous silicon process is used is that such conversion element is suitable as sensor used in the X-ray imaging apparatus, e.g., active element such as the TFTs or the conversion elements can be uniformly formed over a large area; amorphous silicon displays sensitivity in visible light, and X-ray tolerance is strong.

FIGS. 1A and 1B are diagrams illustrating a method of controlling a radiation imaging apparatus according to the present embodiment, and illustrate a method of driving flat plane X-ray detector 111 used in X-ray fluoroscopy. In FIG. 1A, drive states of the flat plane X-ray detector 111 are indicated in a model form by W1, R1, W2, R2. The states indicated at W1 and W2 are waiting operations, i.e., the state TFTs 201 of all pixels are turned OFF. In this state, charges are accumulated in the conversion elements 202. The operation states indicated at R1 and R2 are read-out operations, i.e., an operation to transfer, line by line, charges which have been accumulated in the conversion element 202. The analog image data which has been transferred is converted into digital image data at the read-out circuit 108. The operation states states indicated at W1 and R1 are respectively waiting operation and read-out operation for realizing a frame rate of 30 frames/sec. for time period T11. The operations indicated at W2 and R2 are respectively waiting operation and read-out operation for realizing a frame rate of 15 frames/sec. at time period T12.

Figure 1:
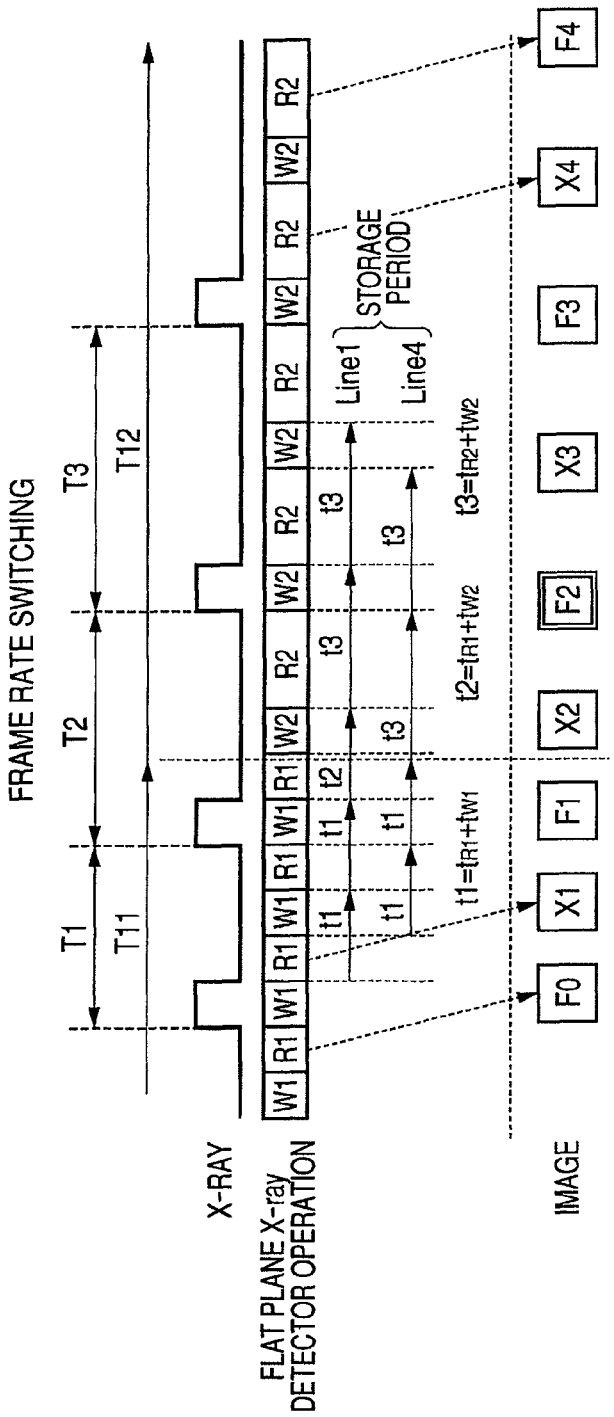
FIGS. 1A and 1B are diagrams illustrating a method of controlling a radiation imaging apparatus according to a first exemplary embodiment.

The period T1 is the irradiation period of X-rays, of 1/30 sec. Until the second irradiation of X-rays, the period of the X-ray irradiation is T1, and is 30/sec. The period T3 is irradiation period of X-rays of 1/15 sec. At the third irradiation of X-rays and irradiations subsequent thereto, the period of the X-ray irradiation is T3, and is 15/sec. The time period T2 between the periods T1 and T3 is a switching time period of period of X-ray irradiation for frame rate switching. In FIG. 1, the X-ray controller 102 can change, in accordance with a period switching signal of X-ray irradiation, the period of X-ray that the X-ray source 101 irradiates. The period of X-ray (radioactive ray) irradiation is an X-ray irradiation period in the case where X-rays are irradiated plural times at a predetermined time interval, and is a time period from starting of the X-ray irradiation to starting of the next X-ray irradiation.

Offset data F0 is frame image data generated by performing waiting operation W1 and read-out operation R1 in the state where no X-rays are irradiated onto the two-dimensional area sensor. Here, in the present invention, the operation in which the two-dimensional area sensor acquires offset data, e.g., F0, refers to the second operation. Next, radiation image data X1 is frame image data generated as the result of the fact that the first X-rays are irradiated onto the two-dimensional area sensor to perform waiting operation W1 and read-out operation R1. Here, in the present invention, the operation in which the two-dimensional area sensor acquires radiation image data, e.g., X1 is called the first operation. Next, offset data F1 is frame image data generated as the result of the fact that no X-rays are irradiated onto the two-dimensional area sensor to perform waiting operation W1 and read-out operation R1. Next, radiation image data X2 is frame image data generated as the result of the fact that the second X-rays is irradiated onto the two-dimensional area sensor to perform waiting operation W1 and read-out operation R1. It is to be noted that, in the present invention, radiation image data X2 acquired immediately before the frame rate is switched by the frame switching signal is called first radiation image data. Moreover, offset data acquired before the frame rate is switched, e.g., F0 or F1 is called the first offset data.

The case where switching of the frame rate is instructed from 30 frames/sec. to 15 frames/sec. by frame switching signal will now be described. At times subsequent thereto, the waiting operation and the read-out operation are respectively W2 and R2. In this case, in the present invention, the period during which frame image data is acquired before the frame rate is switched by the frame switching signal is called the first period, and the period during which frame image data is acquired after the frame rate has been switched is called the second period. Next, offset data F2 is frame image data generated as the result of the fact that no X-rays are irradiated onto the two-dimensional area sensor to perform waiting operation W2 and read-out operation R2. Next, radiation image data X3 is frame image data generated as the result of the fact that the third X-rays are irradiated onto the two-dimensional area sensor to perform waiting operation W2 and read-out operation R2. Next, offset data F3 is frame image data generated as the result of the fact that no X-rays are irradiated onto the two-dimensional area sensor to perform waiting operation W2 and read-out operation R2. Next, radiation image data X4 is frame image data generated as the result of the fact that the fourth X-rays are irradiated onto the two-dimensional area sensor to perform waiting operation W2 and read-out operation R2. Next, offset data F4 is frame image data generated as the result of the fact that no X-rays are irradiated onto the two-dimensional area sensor to perform waiting operation W2 and read-out operation R2. In this case, in the present invention, radiation image data X3 acquired immediately after the frame rate has been switched by frame switching signal is called the second radiation image data. Moreover, offset data acquired after the frame rate has been switched, e.g., F3 or F4 is called second offset data.

At time period T11, data acquisition period (first period) of the flat plane X-ray detector 111 for acquiring single radiation image data is sum of times of waiting operation W1 and read-out operation R1. Moreover, data acquisition period (first period) of the flat plane X-ray detector 111 for acquiring single offset data is also sum of times of waiting operation W1 and read-out operation R1. On the contrary, at time period T12, data acquisition period (second period) of the flat plane X-ray detector 111 for acquiring single radiation image data is sum of times of waiting operation W2 and read-out operation R2. Moreover, data acquisition period (second period) of the flat plane X-ray detector 111 for acquiring single offset data is also sum of times of waiting operation W2 and read-out operation R2. The data acquisition period indicates data acquisition time of single image of the flat plane X-ray detector 111.

In the present embodiment, two images of radiation image data Xn (n is an integer) and offset data Fn (n is an integer) are read out. The radiation image data Xn is generated for a time period during which X-ray is irradiated, and is an image including, as a main part, a charge signal proportional to X-ray incident onto phosphor or conversion element body by the conversion element 202. The offset data Fn is an image containing, as a main part, dark current or image lag of conversion element 202, and offset signal resulting from the read-out circuit 108. Radiation image data Xn is two-dimensional data that the sensor array 110 outputs when X-rays (or radioactive rays) are irradiated. The offset data Fn is two-dimensional data that the plane X-ray detector 111 outputs when no X-rays (radioactive rays) are irradiated. The radiation image data Xn and the offset image Fn are caused to be one set. Thus, a processing to subtract offset data Fn is performed in order to eliminate offset component from the radiation image data Xn. This processing is called offset correction. There are two combinations of subtractions as illustrated in FIG. 1B.

The first method is a method of performing correction by offset data Fn−1 which has been acquired immediately before radiation image data Xn. When corrected image Im is written in the form of the formula, corrected image can be expressed in a manner described below (hereinafter, this offset correction method is described as "before offset correction"):

$$Im=Xn-Fn-1$$

The second method is a method of correcting offset data Fn which has been acquired immediately after radiation image data Xn. The corrected image Im is expressed in the form of the formula as described below (hereinafter, this offset correction method is described as "after offset correction"):

$$Im=Xn-Fn$$

In the present embodiment, switching of the frame rate is performed from the acquisition operation of offset data F2. FIG. 1A illustrates the operation at that time. In the figure, radiation image data X2 is read out thereafter to switch the data acquisition period of the flat plate X-ray detector 111 for the purpose of switching the frame rate from 30 frames/sec. to 15 frames/sec.

Figure 7:
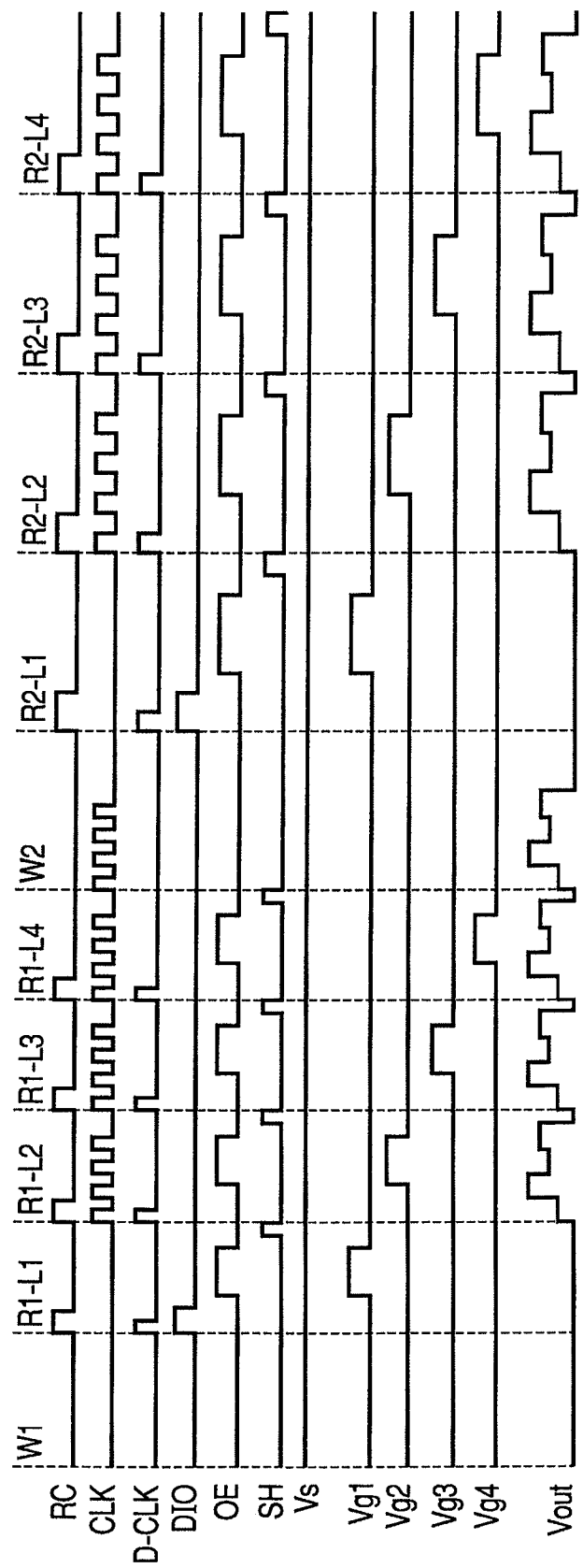
FIG. 7 illustrates a drive timing chart of a flat plane X-ray detector before and after frame rate switching.

Although described in detail later, as illustrated in FIG. 7, in order to obtain an image of one frame, pulses are sequentially delivered to drive wires Vg1 to Vg4. First, the drive wire Vg1 is caused to be at High level. As a result, image signals of conversion elements S11 to S14 of the first Line 1 are read out. Next, the drive wire Vg2 is caused to be at to High level. As a result, image signals of conversion elements S21 to S24 of the second Line 2 are read out. Next, the drive wire Vg3 is caused to be at High level. As a result, the image signals of conversion elements S31 to S34 of the third Line 3 are read out. Next, the drive wire Vg4 is caused to be at High level. As a result, image signals of conversion elements S41 to S44 of the fourth Line 4 are read out. When the drive wires Vg1 to Vg4 change from High level to Low level, the TFT 201 is turned OFF. As a result, the conversion elements S11 to S44 start charge waiting operation W1 or W2. Namely, in the same frame image data, timings of waiting operation W1 or W2 and read-out operation R1 or R2 are changed every line.

As shown in FIG. 1A, at the first row Line 1, read-out operation is performed at the starting part of the read-out operation R1 or R2. After the read-out operation thereof is completed, the next waiting operation W1 or W2 is started. On the contrary, at the fourth Line 4, read-out is performed at the last part of the read-out operation R1 or R2. After the read-out operation thereof is completed, the next waiting operation W1 or W2 is started.

At offset data F1, data acquisition time t1 of the first Line 1 and data acquisition time t1 of the fourth Line 4 are the same. Here, data acquisition time t1 is sum of time tR1 of read-out operation R1 and time tW1 of waiting operation W1. Moreover, in radiation image data X2, the data acquisition time t1 of the first Line 1 and the data acquisition time t1 of the fourth Line 4 are the same. Here, the data acquisition time is the time during which the TFT 201 of the pixel is in OFF state, and is a time during which an electric signal based on charges produced in the conversion element 202 is accumulated into the pixel.

On the contrary, in the offset data F2, data acquisition time t2 of the first Line 1 and data acquisition time t3 of the fourth Line 4 are different from each other. Here, the data acquisition time t2 is sum of time tR1 of the read-out operation R1 and time tW2 of the waiting operation W2. Moreover, the data acquisition time t3 is sum of time tR2 of read-out operation R2 and time tW2 of waiting operation W2.

Further, in radiation image data X3, data acquisition time t3 of the first Line 1 and data acquisition time t3 of the fourth line 4 are the same. Moreover, in offset data F3, data acquisition time t3 of the first Line 1 and data acquisition time t3 of the fourth Line 4 are the same.

The data acquisition period of images F0, X1, F1, X2 is sum of times of waiting operation W1 and read-out operation R1, and is data acquisition period for frame rate of 30 frames/sec. Data acquisition period of images X3, F3, X4, F4 is sum of times of waiting operation W2 and read-out operation R2, and is data acquisition period for frame rate of 15 frames/sec. The period of the waiting operation and the read-out operation for acquiring the offset data F2 is a switching time period of the data acquisition period. The frame rate is inverse number of time interval of a series of operations necessary for acquiring one image for providing an output to an output apparatus such as monitor 105. In concrete terms, the frame rate is inverse number of sum of total time of waiting operation and read-out operation for acquiring radiation image data, and total time of waiting operation and read-out operation for acquiring offset data.

As stated above, there takes place the phenomenon that offset data F2 which have been acquired during switching of data acquisition period are different every line. With respect to the radiation image data and the offset data which are except for the above, data acquisition times of all lines are the same.

Namely, the substantial data acquisition time every one line of the flat plane X-ray detector 111 is a time from the time at which the read-out operation R1 or R2 is completed up to the time at which the next read-out operation R1 or R2 is started. In offset data F2, data acquisition time t1 of the first row Line 1 is sum of time tR1 of read-out operation R1 and time tW2 of waiting operation W2. On the contrary, data acquisition time t3 of the fourth Line 4 is sum of time tR2 of read-out operation R2 and time tW2 of waiting operation W2.

As understood from the above, since the time required for the previous read-out operation R1 or R2 affects the time of waiting operation W1 or W2 of the next frame, data acquisition times of images F2 acquired during switching time period of data acquisition period are different every line. For this reason, this image F2 has shading, and it cannot be said that the picture quality is sufficient.

Moreover, inclination of the shading is not uniform. Accordingly, it is difficult to sufficiently correct such shading. For example, when data acquisition period is switched at the time of starting of acquisition operation of radiation image data, since radiation image data acquired during switching time period has shading, picture quality thereof is not sufficient picture quality as images for operation or diagnosis.

In the present embodiment, there is employed an approach to switch period of an operation for acquiring two-dimensional data of the area sensor between end of read-out operation in acquiring radiation image data and end of read-out operation in acquiring offset data to switch period of the operation for acquiring radiation image data. In other words, the period during which two-dimensional data is acquired is switched at a time period to perform an operation to acquire offset data F2 between an operation for acquiring radiation image data X2 and an operation for acquiring radiation image data X3. By performing such a switching control, an image having shading is caused to be offset data thus to have ability to eliminate acquisition of radiation image data which cannot be used.

Further, in connection with the offset correction of radiation image data, as shown in FIG. 1B, in the before offset correction, correction is performed with respect to radiation image data X3 immediately after data acquisition period has been changed by using offset data F3 which has been acquired immediately thereafter. The control circuit (control unit) 106 performs a control so as to make offset correction, only with respect to radiation image data X3 immediately after data acquisition period has been changed, by using offset data F3 which has been acquired immediately thereafter. Further, the control circuit 106 performs a control, with respect to radiation image data Xn except for the above, by using offset data Fn−1 which has been acquired immediately therebefore.

Furthermore, in the after offset correction, correction is performed, with respect to radiation image data X2 which has been acquired during switching time period of data acquisition period, by using offset data F1 which has been acquired immediately therebefore. The control circuit 106 performs a control so as to make offset correction, only with respect to radiation image data X2 which has been acquired immediately before switching of data acquisition period, by using offset image F1 which has been acquired immediately therebefore. Further, the control circuit 106 performs a control so as to make an offset correction, with respect to radiation image data Xn except for the above, by using offset data Fn which has been acquired immediately thereafter.

Even in the case of both the before offset correction and the after offset correction, the control circuit 106 performs a control so as to make an offset correction, with respect to radiation image data X2 which has been acquired immediately before switching of data acquisition period, by using offset data which has been acquired before acquisition of the radiation image data X2. Control is performed so as to make offset correction by using, e.g., offset data F0 or F1 as offset data which has been acquired before acquisition of the radiation image data X2. In the present invention, such a correction is called the first correction. In the first correction, it is more desirable to use offset data F1 which has been acquired immediately before acquisition of the radiation image data X2. Further, the control circuit 106 performs a control so as to make an offset correction, with respect to radiation image data X3 immediately after data acquisition period has been changed, by using offset data which has been acquired after acquisition of the radiation image data X2. Control is performed so as to make an offset correction by using, e.g., offset data F3 or F4 as offset data which has been acquired after acquisition of the radiation image data X2. In the present invention, such a correction is called the second correction. In the second correction, it is more desirable to use offset data F3 which has been acquired immediately after acquisition of the radiation image data X2.

As stated above, even in the case of either one of correction methods, with respect to radiation image data X2 immediately before switching of data acquisition period and radiation image data X3 immediately after data acquisition period has been changed, correction using offset data F2 which has been acquired in switching of data acquisition period is not performed. These radiation image data are corrected by offset image which has been necessarily acquired under the same condition. For this reason, it is unnecessary to have offset data corresponding to the acquisition condition. As a result, correction is made with good accuracy. There is no possibility that offset data F2 which has been acquired in switching of data acquisition period is used for correction as offset data. For this reason, it can be said that the operation for acquiring offset data F2 is initialization operation of pixel performed for resetting charges accumulated in the pixel.

Figure 5A:
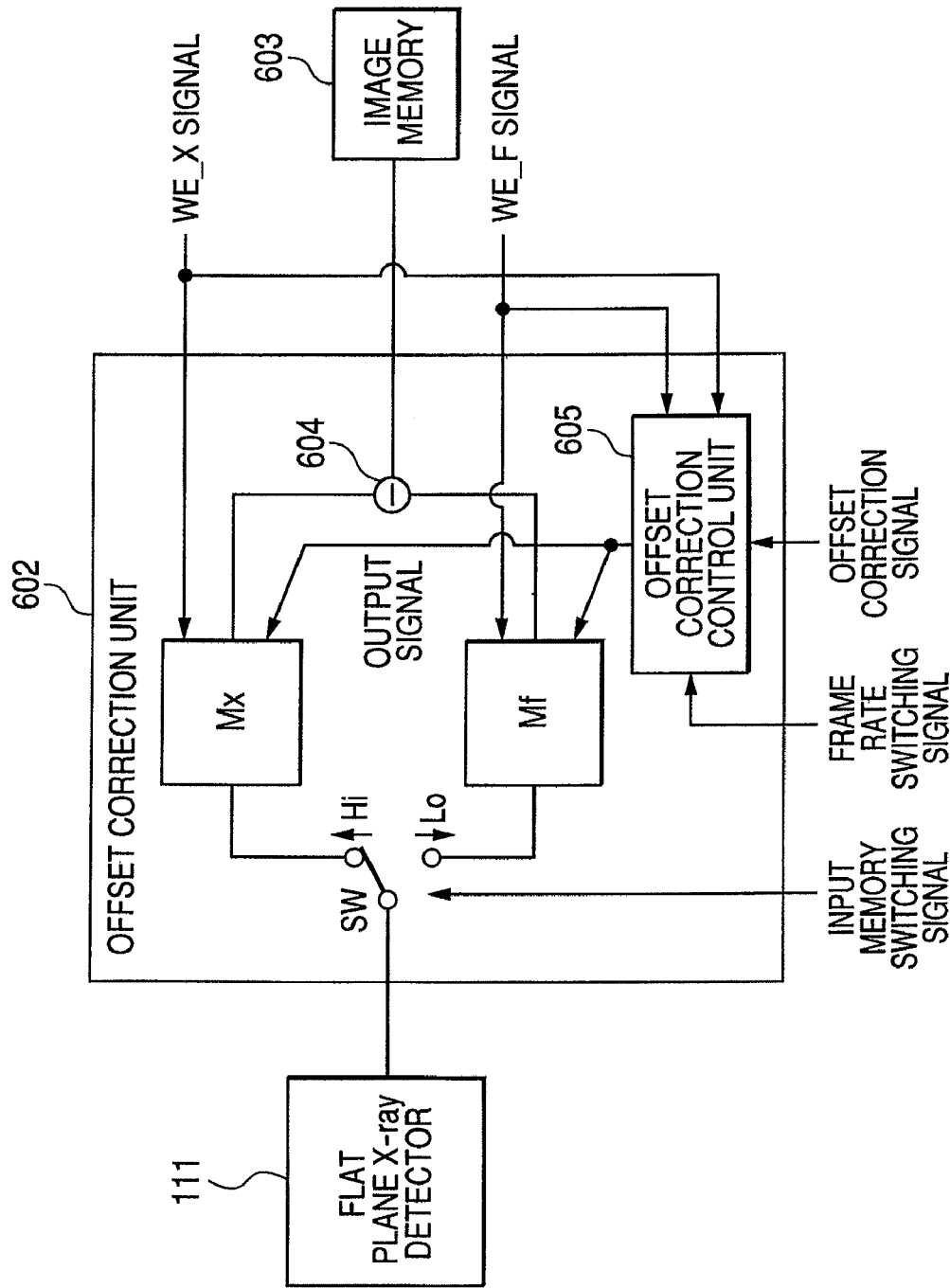

FIGS. 5A and 5B are diagrams illustrating an example of the configuration of offset correction unit 602 for performing the above-mentioned offset correction, and a processing method thereof. Offset correction unit 602 and image memory 603 are provided within image processing and control circuit 106 of FIG. 2. The offset correction unit 602 includes radiation image data memory Mx, offset data memory Mf, switch SW, difference circuit 604, and offset correction control unit 605. The switch SW switches, into memory Mx or Mf, output destination of a digital image signal from the flat plane X-ray detector 111 in accordance with an input memory switching signal. When the input memory switching signal is at High level, radiation image data Xn that the flat plane X-ray detector 111 outputs is output to radiation image data memory Mx. When the input memory switching signal is at Low level, offset data Fn that the flat plane X-ray detector 111 outputs is output into offset data memory Mf.

A WE_X signal is a write enable signal for writing image into radiation image data memory Mx.

When the WE_X signal is at High level, radiation image data Xn is written into radiation image data memory Mx. A WE_F signal is a write enable signal for writing image into offset data memory Mf. When WE_F signal is at High level, offset data Fn is written into offset data memory Mf.

The offset correction control unit 605 outputs an OutPut signal into memories Mx and Mf in accordance with WE_X signal, WE_F signal, frame rate switching signal and an offset correction signal. When a switching pulse is input as a frame rate switching signal, switching of frame rate is instructed from 30 frames/sec. to 15 frames/sec. The receiving time period of this frame rate switching signal is a time period of waiting operation R1 or R2, and read-out operation R1 or R2 of radiation image data Xn of the flat plane X-ray detector 111. When a switching pulse is input, data acquisition period is switched from waiting operation W2 and read-out operation R2 of offset data F2 immediately thereafter.

The offset correction signal is a signal for instructing either before offset correction or after offset correction. The offset correction control unit 605 outputs, to memories Mx or Mf, an OutPut signal at the time of before offset correction, or an OutPut signal at the time of after offset correction in accordance with an offset correction signal. When the OutPut signal is caused to be at High level, an image written in the memories Mx and Mf are output to difference circuit 604.

The difference circuit 604 calculates a difference between output data of two memories Mx and Mf to output its difference image into the image memory 603. The difference image is written into the image memory 603. Thus, it is possible to perform the before offset correction or the after offset correction illustrated in FIG. 1B.

As described above, the offset correction unit 602 is supplied, from the flat plane X-ray detector 111, with an input memory switching signal generated in a manner interlocking with image acquisition from the flat plane X-ray detector 111, a frame rate switching signal notifying that the frame rate has been switched, WE_X signal, and WE_F signal. The WE_X signal and the WE_F signal are respectively write enable signals instructing that image is written into image memories Mx and Mf, and is not written thereinto. The offset correction control unit 605 is supplied with an offset correction signal indicating an offset correction method, a frame rate switching signal notifying that the frame rate is switched, WE_X signal and WE_F signal. The above-mentioned signals are pulses sent in a manner interlocking with drive of the flat plane X-ray detector 111, and is generated by the control circuit 106.

FIG. 5B illustrates waveforms of respective pulses in switching frame rate and the operation of the flat plane X-ray detector 111. An input memory switching signal is generated so that when read-out of radiation image data Xn is started, the input memory switching signal is at High level, while when read-out of offset data Xn is started, the input memory switching signal is at Low level. Radiation image data Xn and offset data Fn are respectively stored into memories Mx and Mf in accordance with an input memory switching signal. The memories Mx and Mf are memories of the FIFO (First In First Out) type. Data which has been first written at the time of write operation can be first read out at the time of read-out operation. When the input memory switching signal is at High level, image data is written into memory Mx. When the input memory switching signal is at Low level, image data is written into the memory Mf. Since the time of High level or the time of Low level of the input memory switching signal is longer than the time period during which image data is sent by time tW1 or tW2 of the waiting operation, WE_F signal and WE_X signal are provided so that no extra data is taken into the memory. When an OutPut signal from the offset correction control unit 605 is input to memories Mx and Mf, image data which have been written in the memories Mx and Mf are sent to the difference circuit 604.

The difference circuit 604 calculates a difference between image data which have been sent from the two memories Mx and Mf to write the difference into the image memory 603. Since the timing at which the memories Mx and Mf send image data to the difference circuit 604 is different by an offset correction signal, in the case where the offset correction control unit 605 performs the before offset correction, the offset correction control unit 605 senses rising of WE_X signal to output an OutPut signal. Further, at the time of after offset correction, the offset correction control unit 605 senses rising of WE_F signal to output an OutPut signal.

In the case where the frame rate is switched, the offset correction control unit 605 performs two kinds of operations in accordance with the offset correction signal. At the time of before offset correction, the offset correction control unit 605 senses falling of WE_F signal so as to use the offset data F3 in place of the offset data F2 as illustrated in FIG. 5B to change a processing so as to output an OutPut signal. At the time of after offset correction, the offset correction control unit 605 senses falling of WE_X signal so as to use offset data F1 in place of offset data F2 to change a processing so as to output an OutPut signal.

Here, it is not necessarily required that the pulse width of the OutPut signal is synchronized with the frame rate. It is sufficient that time required for image transfer operation time is shorter than the time obtained by adding times of waiting operation W1 or W2 and the read-out operation R1 or R2. Moreover, the data transfer rate that the circuit within the offset correction unit 602 has is optimized in view of the time required for image processing after offset correction, or the maximum frame rate that the flat plane X-ray detector 111 can drive.

By the above-mentioned processing, it is possible to process offset data F2 having shading without using such offset data F2 for correction to perform offset correction of radiation image data by using a suitable offset data.

Here, as the offset correction unit 602, there may be used IC in which memory such as DRAM, SDRAM or SRAM and CPU are combined, or IC having the above-mentioned functions.

The previously described method of switching offset correction followed by frame rate switching can be applied to both the case where switching is performed in a direction where the frame rate is decreased, which is illustrated in FIG. 5B, and the case where switching is performed in a direction where the frame rate is increased, which is illustrated in FIG. 6. FIG. 7 is a diagram illustrating a processing method by the offset correction unit 602 in the case where switching is performed in a direction where the frame rate is increased. When a pulse of the frame rate switching signal is input, the frame rate is switched from 15 frames/sec. to 30 frames/sec. The processing of FIG. 6 is similar to the processing of FIG. 5B.

Moreover, the time period during which the switching signal of the frame rate is not accepted is the time period during which offset data Fn is acquired, and the time period from the time at which the data acquisition period has been changed until the first offset data F3 is written into the memory Mf. The frame rate can be switched within 1 to 2 frames. Thus, frame rate switching instruction can be arbitrarily and continuously given from user (worker) or an apparatus.

The control circuit 106 performs a control so as to switch data acquisition period of the flat plane X-ray detector 111 in accordance with instruction of an arbitrary timing of user.

Moreover, the control circuit 106 performs a control so as to switch data acquisition period of the flat plane X-ray detector 111 in accordance with the frame rate switching signal.

FIG. 7 is a drive timing chart of the flat plane X-ray detector 111 before and after the frame rate switching. For brevity of description, the case of the circuit configuration of the flat plane X-ray detector 111 of 4×4 pixels illustrated in FIG. 2 is illustrated as an example. However, the number of pixels is not limited to 4×4. In addition, the number of read-out circuits 108, the number of A/D converters 210, the number of signal wires Sig 1 to Sig 4 in a column direction, and the number of vertical drive circuits 112 are not limited to those members of circuit components illustrated in FIG. 2.

In order to obtain single radiation image data and offset image, after waiting operation W1 or W2 is performed, read-out operation R1 or R2 is performed. The waiting operation corresponds to the time periods of W1 and W2 illustrated in FIG. 7, and is an operation in which voltage Vs of the sensor power source 203 is set to a desired value to turn the TFT 201 OFF in the state where the conversion element 202 is permitted to perform photoelectric conversion. At this time, the integration amplifier 205 within the read-out circuit 108 may be placed in reset state.

The operation for reading out charges accumulated in the conversion element 202 corresponds to a time period from R1-L1 to R1-L4 and a time period from R2-L1 to R2-L4. The read-out operation R1 is a time period from R1-L1 to R1-L4, and the read-out operation R2 is a time period from R2-L1 to R2-L4. R1-L1 and R2-L1 indicate read-out operation and the time therefor of the first Line 1, R1-L2 and R2-L2 indicate read-out operation and the time therefor of the second Line 2, R1-L3 and R2-L3 indicate read-out operation and the time therefor of the third row Line 3, and R1-L4 and R2-L4 indicate read-out operation and the time therefor of the fourth Line 4.

In the read-out operation R1-L1 of the first Line 1, the feedback part of the integration amplifier 205 is short-circuited by RC signal to reset an output of the integration amplifier 205. By employing such an approach, the influence based on charges taking place at the time of the previous operation is eliminated.

Next, D-CLK signal and DIO signal are output to vertical drive circuit 112, a voltage Vcom is delivered only to drive wire Vg1 of the first Line 1, and voltage Vss is delivered to drive wires Vg2 to Vg4 of other lines. An OE signal is caused to be at High level after RC signal has been brought into Low level to apply voltage Vcom to drive wire Vg1 of the first Line 1 to turn the TFT 201 of the first row Line 1 ON to transfer charges accumulated in the conversion element 202 to the integration amplifier 205.

After the TFT 201 is turned ON for a sufficient time, voltage Vss is applied to drive wire Vg 1 of the first Line 1 to turn the TFT 201 OFF. Further, after the TFT 201 is turned OFF, a SH signal is caused to be at High level to allow the sampling and holding circuit 207 to be operative to hold an output of the integration amplifier 205.

A signal which has been held in the sampling and holding circuit 207 is output to an A/D converter 210 by multiplexer 208 at the time of read-out operation of the next line so that the signal thus output is converted into digital data. At times subsequent thereto, pulse of voltage Vcom is sequentially applied to drive wires Vg2 to Vg4 to perform read-out operations R1-L2 to R1-L4 of the second to the fourth lines similarly to the read-out operation R1-L1 of the first line. By repeating the above-mentioned read-out operation by the number of drive wires, read-out operation of all pixels can be performed.

When a pulse of the frame rate switching signal is input, data acquisition period is changed from the read-out operation R2. Until the read-out operation R1, data acquisition period is short. From the read-out operation R2, the data acquisition period becomes long. The read-out operations R2-L1 to R2-L4 are performed similarly to the above-mentioned read-out operations R1-L1 to R1-L4.

When switching of the frame rate is instructed, the times of read-out operations R1, R2, or times of waiting operations W1, W2 are changed in the flat plane X-ray detector 111. As the simplest method, there is a method of fixing times of read-out operations R1, R2 so that such time becomes equal to operation time (shortest time) at the time of the maximum frame rate (e.g., 30 frames/sec.) to change only storage times W1, W2 in accordance with the frame rate. However, when times of read-out operations R1, R2 are shortened, charges accumulated in the conversion element 202 cannot be sufficiently transferred from the problem of charge transfer ability of the TFT 201. Moreover, since it is required to shift the frequency band of LP (Low-Pass Filter) within the read-out circuit 108 to the higher frequency band side, noise would be into a signal. Further, since the reset time of the integration amplifier 205 is insufficient, noise would be mixed into an image. By the above-mentioned phenomenon, signal-to-noise ratio of an image is lowered. In addition, in order to turn the TFT 201 OFF thereafter to immediately perform sample and hold operation, voltage change of drive wire is superimposed on a image signal as offset.

From facts stated above, employment of a method of allowing read-out time to remain short, although the frame rate is small so that read-out time can be sufficiently taken, does not provide merit. It is desirable from a viewpoint of image to suitably change the read-out time in accordance with the frame rate.

With respect to drive timing, as illustrated in FIG. 7, for example, there may be employed an approach to merely multiply pulses of respective signals by a constant, or there may be provided, for every frame rate, a drive pattern optimized so that the signal-to-noise ratio becomes high to such a degree that the system does not become complicated.

For example, read-out drive patterns for 1 frame/sec., 7.5 frames/sec., 10 frames/sec., 15 frames/sec., 20 frames/sec. and 30 frames/sec. may be provided. Thus, complying with the frame rate therebetween may be performed by change of storage times W1, W2.

As described above, in accordance with the present embodiment, the problem that image acquired during switching time period of data acquisition period is not used depending upon difference of storage time at the time of switching frame rate is avoided to perform correction by an offset image acquired immediately therebefore or immediately thereafter. Thus, radiation image data can be corrected irrespective of difference of gain or storage time, and difference of read-out method.

The present embodiment is a simple system in which even if no correction data is provided every switching pattern of frame rate as in the case of the above-mentioned Patent Literatures 1 and 2, two image memories Mx and Mf are provided to perform offset correction in synchronism with driving of fluoroscopic system. The present embodiment can comply with various frame rate switching operations. Moreover, the present embodiment has the merit that offset correction is performed by offset data which is similar to radiation image data acquisition in terms of time, and is the same acquisition condition so that offset correction having high accuracy can be made.

It is to be noted that the number of pixels is not limited to 4×4 in the present embodiment, but the number of read-out circuits, the number of A/D converters, the number of signal wires in a column direction, and the number of vertical drive circuits are not limited to the numbers of circuit components illustrated in FIG. 2.

Further, as the conversion element in the present embodiment, either one of three kids of conversion elements illustrated in FIGS. 4A to 4C may be used. The conversion element in the present embodiment may be applied irrespective of signal amplifying method, analog-to-digital conversion method, and/or the number of read-out circuits or A/D converters. In addition, while the offset data F2 is converted from analog image data to digital image data by read-out circuit 108 in the present embodiment, the present invention is not limited to such implementation. The configuration such that read-out of an electric signal corresponding to offset data F2 is performed by the two-dimensional area sensor, but no offset data F2 is acquired without allowing the read-out circuit 108 to be operative is also within the scope of the present invention.

Second Exemplary Embodiment

Figure 8A:
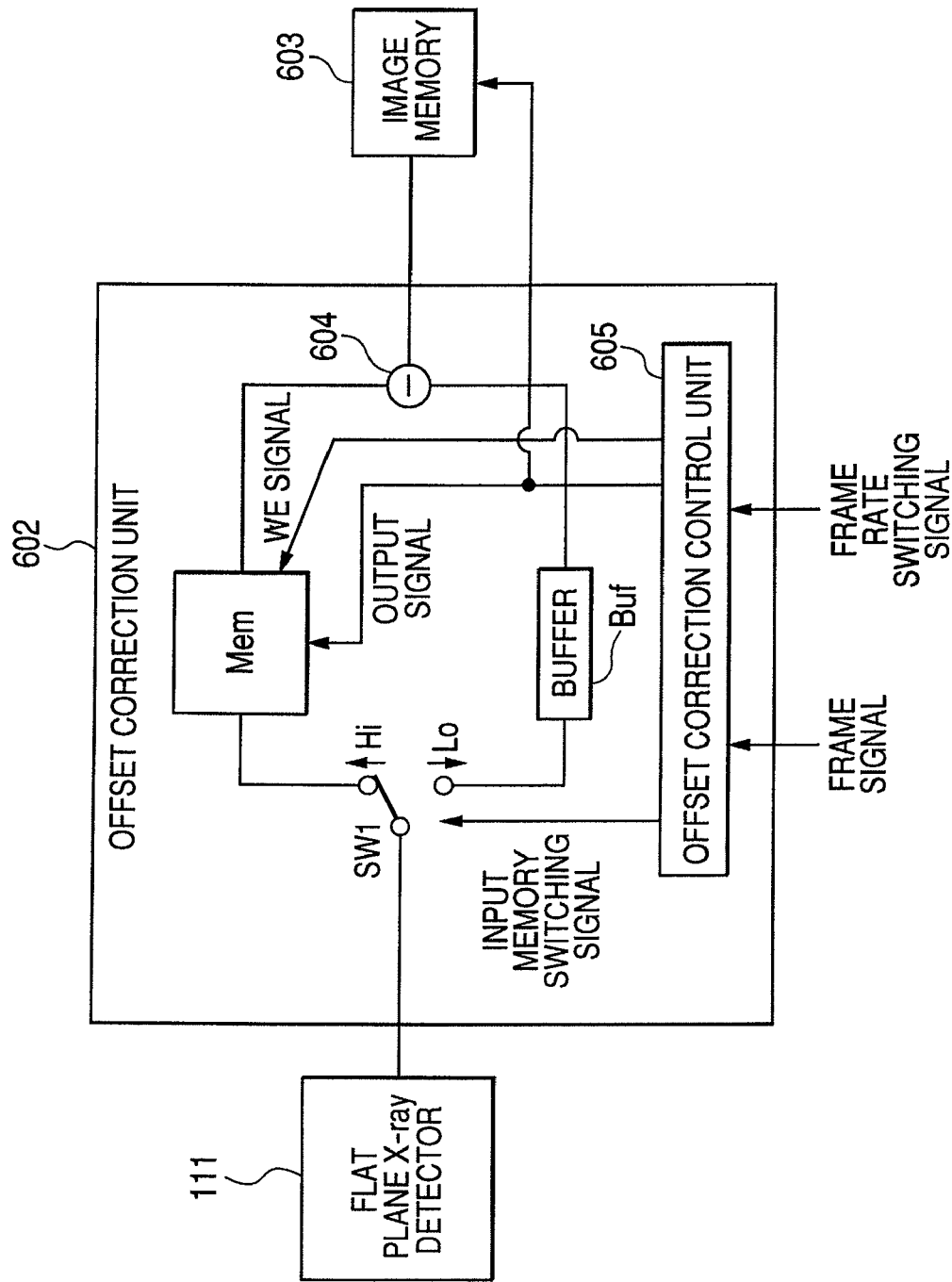

FIGS. 8A and 8B are diagrams illustrating an example of the configuration of offset correction unit 602 according to the second exemplary embodiment of the present invention and a processing method therefor. The point of the present embodiment different from the first exemplary embodiment will now be described. The offset correction unit 602 of FIG. 8A differs from the offset correction unit 602 of FIG. 5A in that the offset correction unit 602 is configured by using image memory Mem corresponding to one image and buffer Buf which can hold data corresponding to one line of the flat plane X-ray detector 111. When the input memory switching signal is at High level, switch SW1 connects an output of the flat plane X-ray detector 111 to memory Mem. When the input memory switching signal is at Low level, the switch SW1 connects an output of the flat plane X-ray detector 111 to buffer Buf.

Moreover, the offset correction unit 602 of FIG. 8A differs from the offset correction unit 602 of FIG. 5A in that a signal which is input from the external in order to perform offset correction is a frame rate switching signal, and a frame signal which is synchronous with radiation image data and offset data. From these two signals, the offset correction control unit 605 generates an input memory switching signal, a WE signal for controlling write operation into memory Mem, and OutPut signal.

FIG. 8B illustrates timing of offset correction of offset correction unit 602 of FIG. 8A. In the present embodiment, only before offset correction can be performed from a viewpoint of the configuration of offset correction unit 602.

In the state before the frame rate is switched, at the time of acquiring offset data Fn, the input memory switching signal is caused to be at High level to output offset data Fn of the flat plate X-ray detector 111 to the memory Mem. At the time of acquiring radiation image data Xn, the input memory switching signal is caused to be at Low level to output, a line by line, radiation image data Xn of the flat plane X-ray detector 111 to the buffer Buf. When the OutPut signal is caused to be at High level, offset data Fn stored in the memory Mem is output to difference circuit 604. The difference circuit 604 calculates a difference between radiation image data Xn which is output from buffer Buf and offset data Fn which is output from memory Mem to write the difference thus calculated into image memory 603. By employing such an approach, the before offset correction is performed.

When the frame rate switching signal is input, the offset correction control unit 605 allows the WE signal to be placed at Low level so as not to acquire offset data F2 having shading. Next, the input memory switching signal and the WE signal are caused to be at High level so as to take radiation image data X3 into memory Mem to write the radiation image data X3 into the memory Mem. Finally, in taking offset data F3 into the buffer Buf, in a manner opposite to the above, the input memory switching signal is caused to be at Low level to output offset data F3 to the buffer Buf. Simultaneously therewith, the offset correction control unit 605 allows OutPut signal to be at High level in synchronism with the frame signal. Thus, radiation image data X3 is output from the memory Mem to the difference circuit 604. At time subsequent thereto, the before offset correction similar to the above is performed.

By the above-mentioned operation, immediately after the data acquisition period (frame rate) is changed, there results an operation for performing after offset correction. Thus, offset correction without using offset data F2 having shading at offset can be performed. Here, only when OutPut signal is at High level, the image memory 603 holds a signal of the difference circuit 604. When the OutPut signal is at Low level, the image memory 603 does not hold data. In accordance with the present embodiment, the capacity of the memory can be reduced. Thus, the cost of the offset correction unit 602 can be reduced. It is to be noted that, in the present embodiment, offset data F2 is converted from analog image data into digital image data at the read-out circuit 108, and the offset correction control unit 605 performs a control so as not to acquire offset data F2. However, the invention of this Application is not limited to such implementation. The configuration, in which read-out of an electric signal corresponding to offset data F2 is performed by the two-dimensional area sensor, but no offset data F2 is acquired without allowing the read-out circuit 108 to be operative, may be also included in the invention of this Application.

Third Exemplary Embodiment

Figure 9:
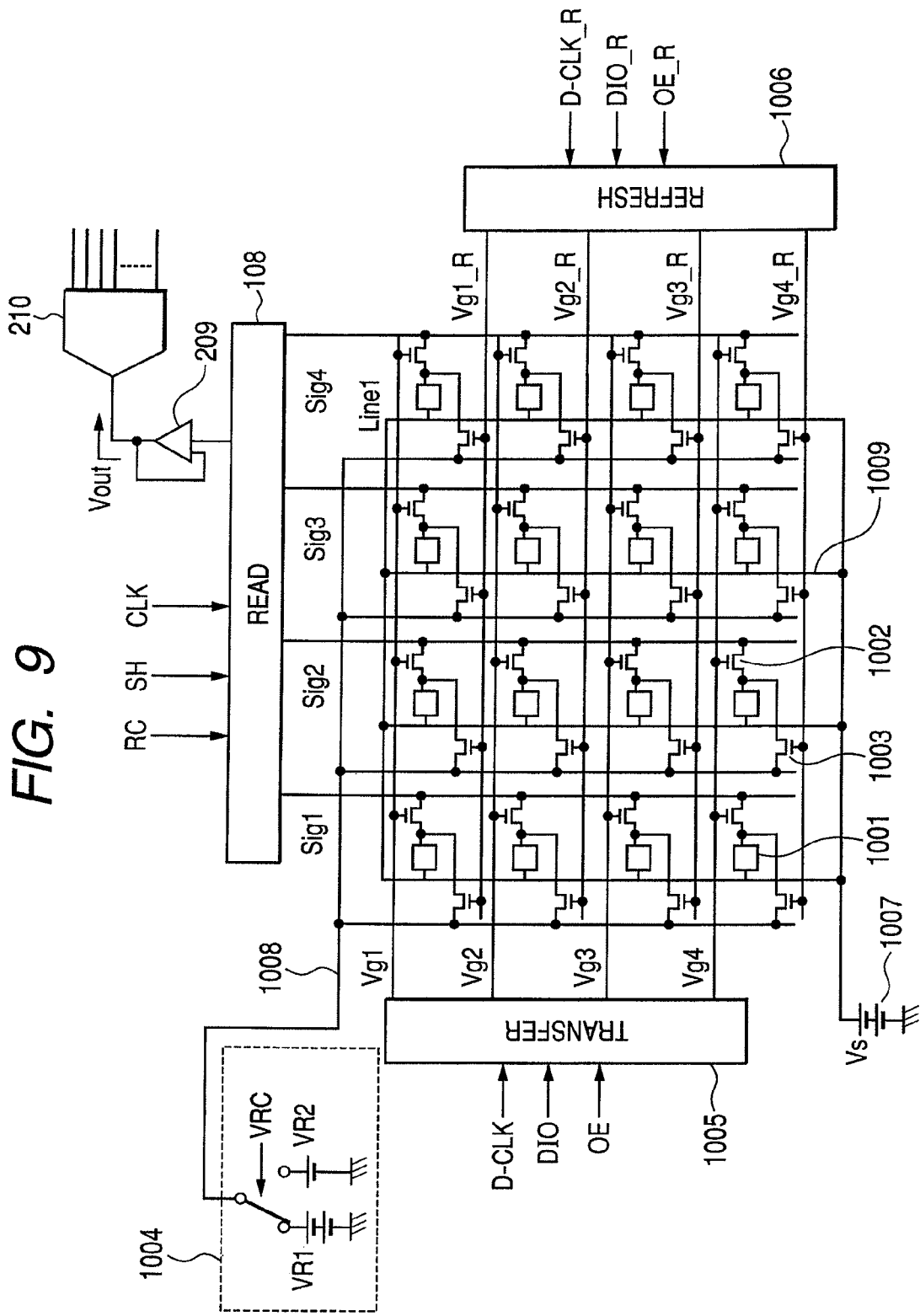
FIG. 9 is a circuit diagram illustrating an example of the configuration of a flat plane X-ray detector according to a third exemplary embodiment of the present invention.

FIG. 9 is a circuit diagram illustrating an example of the configuration of flat plane X-ray detector 111 according to the third exemplary embodiment of the present invention, and illustrates a circuit diagram of flat plane X-ray detector 111 using MIS type conversion element 1001 as the conversion element. The point of the present embodiment different from the first exemplary embodiment will now be described. The flat plate X-ray detector 111 includes MIS type conversion elements 1001, transfer TFTs 1002, refreshing TFTs 1003, a refreshing power source 1004, a transfer vertical drive circuit 1005, a refreshing vertical drive circuit 1006, a sensor bias power source 1007, a refreshing line 1008, and sensor bias lines 1009.

In the MIS type conversion element 1001, as previously described with reference to FIG. 4B, there is the problem that when charges are accumulated at interface between A-Si layer 308 serving as photoelectric conversion layer and insulating layer 307 so that accumulation quantity of the charges is increased, voltages on both ends of the A-Si layer 308 are equal to each other so that photoelectric conversion cannot be performed.

To solve the problem, two kinds of power sources of photoelectric conversion power source 1007 and refreshing power source 1004 having a voltage lower than that of the power source are prepared as sensor bias power source of the sensor array thus to sweep out charges accumulated on the interface by a refreshing operation to periodically switch voltage.

In FIG. 9, in addition to transfer TFT 1002 for transferring charges accumulated in the conversion element 1001 to integration amplifier within the read-out circuit 108, there are provided refreshing TFTs 1003 for applying a voltage from the refreshing power source 1004 to the conversion element 1001. Thus, there is employed a configuration in which an electric potential of the insulating layer side of the sensor electrode is changed to perform refreshing operation.

The feature of this configuration is that refreshing operation of conversion elements 1001 can be performed every one line in a lateral direction to perform refreshing operation in parallel to read-out operation. Vertical drive circuit 1006 for driving the refreshing TFTs 1003 is newly provided. The vertical drive circuit 1006 is supplied with D-CLK_R signal, DIO_R signal and OE_R signal to deliver a voltage to drive wires Vg1_R, Vg2_R, Vg3_R and Vg4_R. These drive wires Vg 1_R, Vg 2_R, Vg 3_R, Vg 4_R are respectively connected to gates of refreshing TFTs 1003 of the Line 1 to Line 4.

Figure 10:
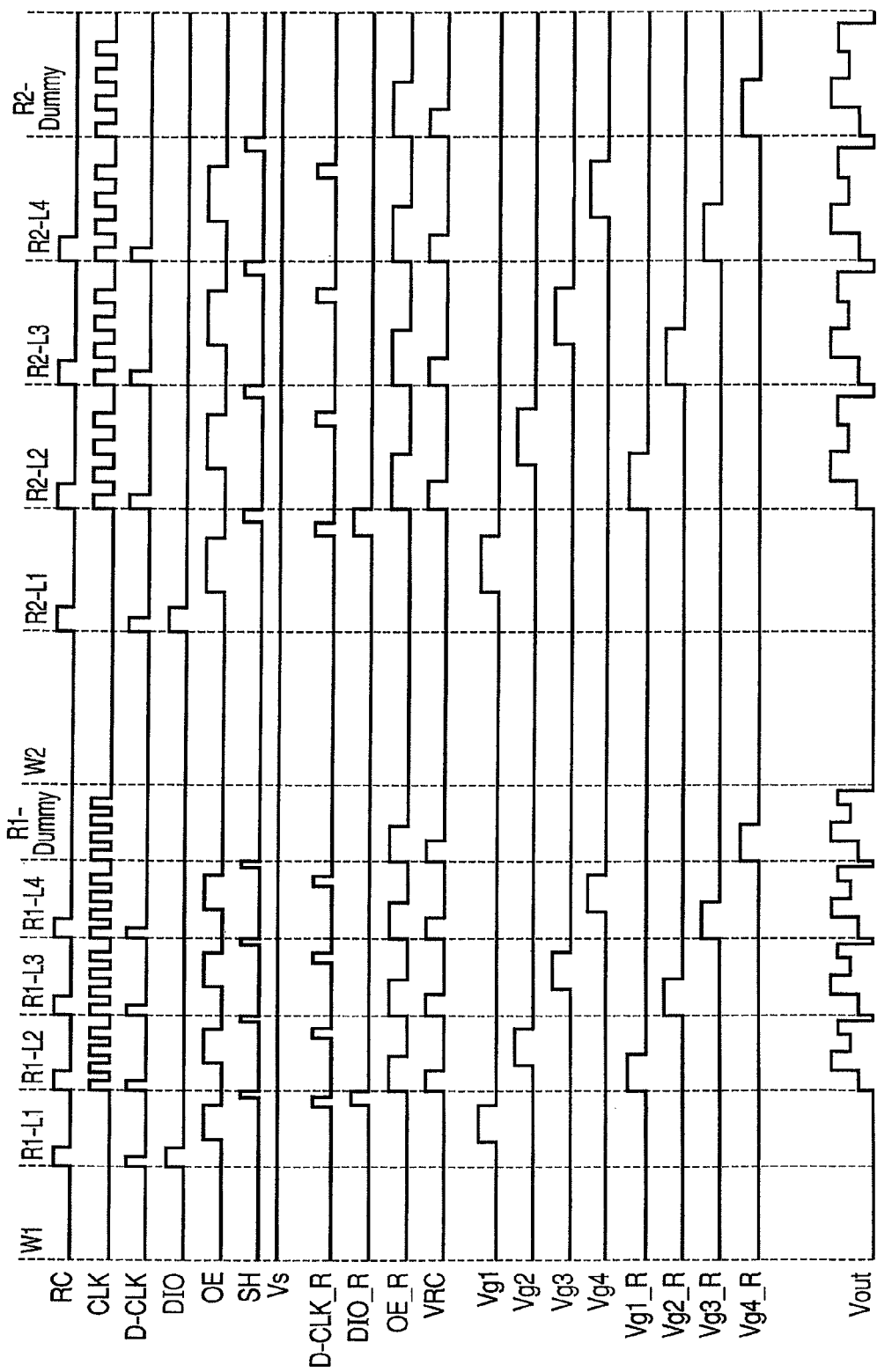
FIG. 10 illustrates a drive timing chart of the flat plane X-ray detector of FIG. 9.

FIG. 10 is a drive timing chart of the flat plane X-ray detector 111 of FIG. 9. Here, the operations of the transfer TFT 1002 and read-out circuit 108 are the same as those which have been described in the first exemplary embodiment.

In order that the refreshing operation is performed in a manner delayed by one line from read-out operation, DIO_R signal and D-CLK_R signal are delivered in the state delayed relative to DIO signal and D-CLK signal delivered to transfer vertical drive circuit 1005. When pulses are sequentially delivered to drive wires Vg1 to Vg4 to turn the transfer TFT 10020N, charges can be transferred. With respect to the row in which transfer of charges has been completed, for a time period during which charges on the next line have been read out, pulses are sequentially delivered to drive wires Vg1_R to Vg4_R to turn the refreshing TFT 10030N. Substantially simultaneously therewith, voltage on the refreshing line 108 is switched into VR1 to sweep out charges accumulated in the conversion element 1001 to sensor bias line 1009.

Next, voltage of the refreshing line 1008 is switched into VR2 thereafter to turn the refreshing TFTs 1003 OFF. By the above-mentioned operation, refreshing operation of one line is completed. In order to perform refreshing operation of all pixels, it is sufficient to perform refreshing operation of all lines in synchronism with read-out operations of respective lines. Thus, as illustrated in FIG. 10, at the last time of single image, operations only inclusive of refreshing operation expressed as R1-Dummy and R2-Dummy take place. Thus, read-out time corresponding to one line is elongated as compared to FIG. 8.

From facts stated above, even with sensor array for which refreshing operation is required, as the operation itself, images can be continuously obtained similarly to the two-dimensional area sensor as illustrated in FIG. 2 which has been previously described. Moreover, even in the case where the frame rate is switched, the operation is similar to that of the first exemplary embodiment. Therefore, the present embodiment may be applied even to the two-dimensional area sensor using MIS type conversion element 1101.

Fourth Exemplary Embodiment

Figure 11A:
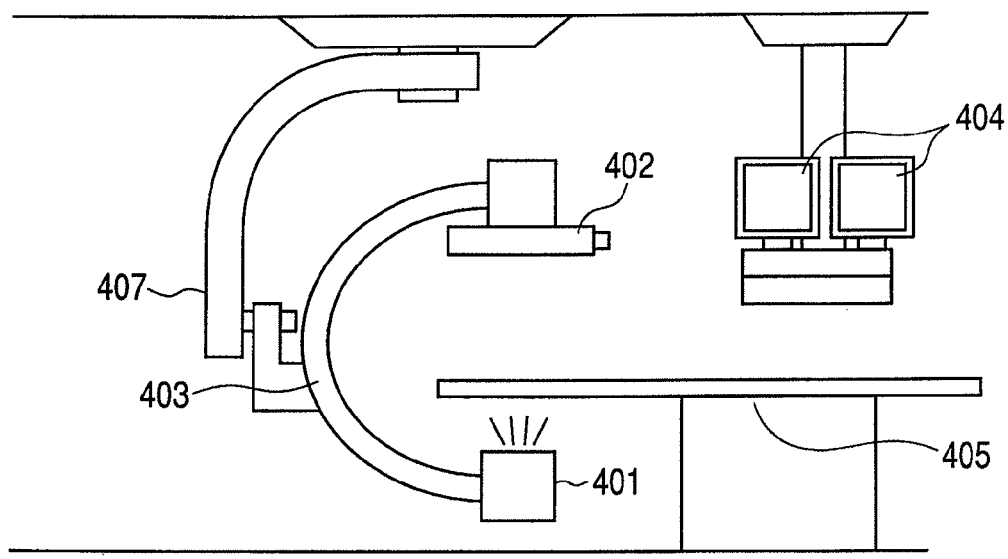
FIGS. 11A and 11B are diagrams illustrating an example of the configuration of a digital radiation (X-ray) imaging system according to a fourth exemplary embodiment of the present invention.
Figure 11B:
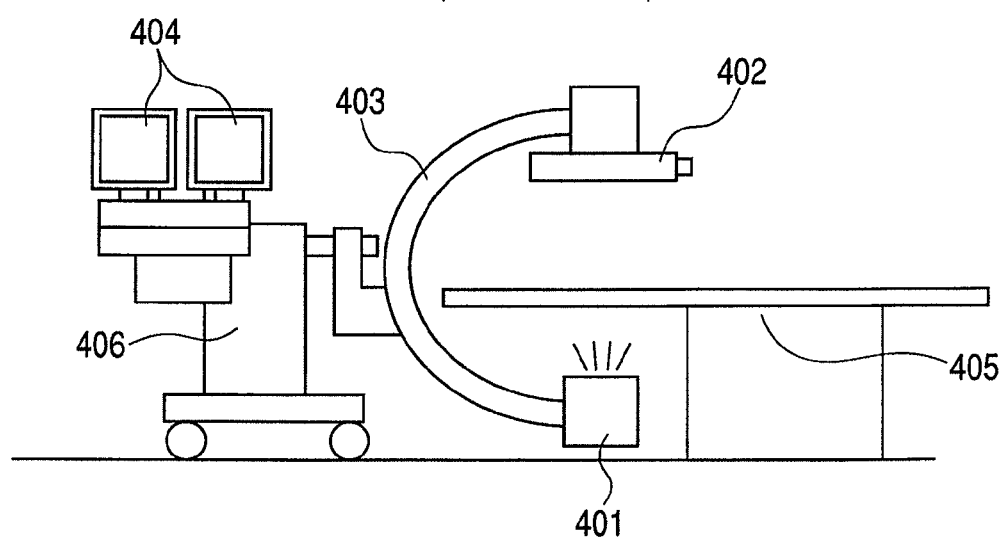

FIGS. 11A and 11B are diagrams illustrating an example of the configuration of digital radiation (X-ray) imaging system according to the fourth exemplary embodiment of the present invention. The digital radiation imaging system of the present embodiment is directed to a fluoroscopic system as an applied example of flat plane X-ray detector 111 using the sensor array according to any one of first to the third exemplary embodiments.

FIG. 11A illustrates a digital radiation imaging system of the C-arm (type of running on ceiling), and FIG. 11B illustrates a digital radiation imaging system of the C-arm (mobile type). This digital radiation imaging system includes an X-ray source 401, a flat plane X-ray detector 402, a C-arm 403, a monitor 404, a bed 405, a truck 406 (mobile fluoroscopic system), and a suspending unit 407. In FIG. 11B, the X-ray source 401 and the flat plane X-ray detector 402 are disposed on both sides of the C-type suspending instrument, and the C-type suspending instrument is fixed on the movable truck 406.

The fluoroscopy is X-ray moving picture radiographing. Thus, radiographing is continuously performed at an X-ray dosage per one image lower by one digit or more at a low resolution as compared to still image. In the fluoroscopic apparatus, as illustrated in FIGS. 11A and 11B, flat plane X-ray detector 402 and X-ray source (X-ray generator) 401 which are adapted for obtaining radiation image data are oppositely disposed. The fluoroscopy can mainly perform monitoring in carrying out catheter insertion or surgical operation, and diagnosis of lesions of vessels or organs, and can satisfy a requirement to perform radiographing of an object from various angles.

Moreover, as a high sensitivity X-ray detector, there is a system in which photomultiplier which is called Image Intensifier (I•I) and CCD camera are combined. However, in recent years, since realization of high sensitivity•realization of high speed operation of the flat plane X-ray detector is developed so that performance can been improved until fluoroscopy can be sufficiently performed, fluoroscopic apparatus using the flat plane X-ray detector can be put into practice.

In the case of the flat plane X-ray detector, since the apparatus itself becomes compact as compared to the I•I and the CCD camera system, radiographing can be performed at an angle where radiographing was conventionally difficult. Thus, the flat plane X-ray detector has the excellent feature in which there is no distortion of image, and the contrast is high.

As stated above, in the first to fourth exemplary embodiments, there are provided a frame to perform read-out operation for acquiring radiation image data, and a frame to perform read-out operation for acquiring offset data, which is continuous thereto, to correct radiation image data by using such offset data. Further, since storage times of frames acquired during switching time period of data acquisition period for acquiring two-dimensional data are different every respective lines, switching of the data acquisition period is performed at the time of acquiring offset data. Further, offset correction of radiation image data X2, X3 immediately before and immediately after switching of the data acquisition period can be performed by respectively using offset data F1, F3 which have been acquired immediately before and immediately after switching of the data acquisition period. By an operation as stated above, even if storage time, the number of read-out lines and gain are changed, offset of radiation image data can be precisely corrected by offset image which has been acquired under the same condition as that of radiation image data.

The flat plane X-ray detector 111 is a two-dimensional area sensor for performing, a line by line, read-out operation of electric signals accumulated in a plurality of pixels arranged in a matrix to convert radiation (X-ray) into an electric signal to output two-dimensional data. The flat plane X-ray detector 111 is adapted so that the two-dimensional area sensor performs read-out operation under irradiation with a radiation with respect to the two-dimensional area sensor to thereby acquire radiation image data, and to perform read-out operation under non-irradiation with radiation with respect to the two-dimensional area sensor thus to have ability to acquire offset data. The control circuit (control unit) 106 performs switching of period for acquiring two-dimensional data of the flat plane X-ray detector 111 between end of read-out operation for acquiring radiation image data F2 and end of read-out operation capable of acquiring offset data F2 for a switching time period T2 of period of irradiation with radiation. Thus, control is performed so as to make a switching of period for acquiring radiation image data.

In accordance with the first to fourth exemplary embodiments, quantity of offset correction data, which is to be held, can be reduced. Thus, the system can be simplified, and the cost of the system can be reduced. Further, since offset data acquired on the real time basis is used, switching can be immediately performed from the frame rate switching instruction. Thus, interlocking operation with an external apparatus can be realized, and reduction in dosage of exposure to radiation based on fine frame rate management can be effectively performed. As a result, convenient and inexpensive radiation imaging apparatus can be realized.

Further, the configuration of a fluoroscopic apparatus using a flat plane X-ray detector capable of freely changing the frame rate can be simplified. Further, even in the case of continuously switching the frame rate, offset correction can be performed. Furthermore, the dosage of exposure to radiation of a patient is reduced, and the frame rate can be finely adjusted. In addition, fluoroscopy can be performed while taking synchronization with various apparatuses. Thus, reduction in dosage of exposure to radiation and radiographing by CT can be performed.

It is to be noted that the above-mentioned exemplary embodiments all only illustrate examples of embodiment in carrying out the present invention, and therefore the technical scope of the present invention should not be restrictively interpreted by these exemplary embodiments. Namely, the present invention may be carried out in various forms without departing from the technical idea thereof and main features thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-023385, filed Feb. 1, 2007, which is hereby incorporated by reference herein in its entirety.

What is claimed is:

1. A radiation imaging apparatus comprising:
an area sensor for reading out an electric signal accumulated in a plurality of pixels arranged in a matrix, line by line, wherein the area sensor operates in a first operation for deriving radiation image data by reading a signal accumulated during irradiation with radiation, and a second operation for deriving offset data by reading a signal accumulated during non-irradiation with radiation, alternately, and wherein a frame rate is an inverse number of a sum of a time for the first operation and a time for the second operation; and
a control unit for controlling the area sensor,
wherein each of the first and second operations includes a waiting operation for accumulating the electric signal in the plurality of pixels of the area sensor and a read-out operation for reading out the electric signal accumulated in the plurality of pixels of the area sensor, and
wherein the control unit switches the frame rate after the end of the read-out operation in the first operation and before an end of the read-out operation in the second operation which is continuous to the end of the read-out operation in the first operation.

2. The radiation imaging apparatus according to claim 1, further comprising:
a correction unit for correcting the radiation image data, wherein the control unit controls the correction unit so that the correction unit does not correct the radiation image data based on the offset data which is acquired during switching of the frame rate, said offset data being data derived by the second operation operated during the time period from the end of the read-out operation in the first operation until the end of the read-out operation in the second operation.

3. The radiation imaging apparatus according to claim 2, wherein the control unit controls the correction unit so that the correction unit corrects first radiation image data based on first offset data, and corrects second radiation image data based on a second offset data, the first radiation image data being radiation image data derived immediately before switching of the frame rate, the first offset data being offset data derived before deriving the first radiation image data, the second radiation image data being radiation image data derived immediately after switching of the frame rate, and the second offset data being offset data derived after deriving of the second radiation image data.

4. The radiation imaging apparatus according to claim 3, wherein the control unit controls the correction unit so that the correction unit corrects only the second radiation image data based on the second offset data, and corrects the other radiation image data including the first radiation image data based on the offset data derived before deriving the other radiation image data.

5. The radiation imaging apparatus according to claim 3, wherein the correction unit corrects only the first radiation image data based on the first offset data, and corrects the other radiation image data including the second radiation image data based on the offset data derived after deriving the other radiation image data.

6. A radiation imaging system comprising:
a radiation imaging apparatus according to claim 1; and
a radiation generator for generating radiation,
wherein the control unit switches a period of the radiation generated by the radiation generator.

7. The radiation imaging apparatus according to claim 1, wherein each of the plurality of pixels comprises conversion element for converting a radiation into an electric charge and switching element for outputting the electric signal according to the electric charge, the waiting operation in the first and second operation is an operation which the switching elements of the plurality of the pixels of the area sensor are turned off, and the read-out operation in the first and second operation is an operation which the switching elements of the plurality of the pixels of the area sensor output the electric signal line by line.

8. A radiation imaging apparatus comprising:
an area sensor for reading out an electric signal accumulated in a plurality of pixels arranged in a matrix, line by line, to derive two-dimensional data, wherein the area sensor operates in a first operation for deriving radiation image data by reading during an irradiation with radiation, and a second operation for deriving offset data by reading during non-irradiation with the radiation, alternately, and wherein a frame rate is an inverse number of a sum of a time for the first operation and a time for the second operation; and a control unit for controlling the area sensor, wherein each of the first and second operations includes a waiting operation for accumulating the electric signal in the plurality of pixels of the area sensor and a read-out operation for reading out the electric signal accumulated in the plurality of pixels of the area sensor, and wherein the control unit switches the frame rate, from a first period of the first operation into a second period different from the first period, during a time period of the waiting operation and the read-out operation in the second operation which is continuous to the end of the read-out operation in the first operation.

9. The radiation imaging apparatus according to claim 8, further comprising:

a correction unit for correcting the radiation image data, wherein the control unit controls the correction unit so that the correction unit does not correct the radiation image data based on the offset data which is acquired during switching of the frame rate, said offset data being data derived by the second operation operated during the time period the control unit switches the frame rate.

10. The radiation imaging apparatus according to claim 9, wherein the control unit controls the correction unit so that the correction unit corrects first radiation image data based on first offset data, and corrects a second radiation image data based on second offset data, the first radiation image data being radiation image data derived immediately before switching of the frame rate, the first offset data being offset data derived before deriving of the first radiation image data, the second radiation image data being radiation image data derived immediately after switching of the frame rate, and the second offset data being offset data derived after deriving of the second radiation image data.

11. The radiation imaging apparatus according to claim 10, wherein the control unit controls the correction unit so that the correction unit corrects only the second radiation image data based on the second offset data, and corrects the other radiation image data including the first radiation image data based on the offset data derived before deriving the other radiation image data.

12. The radiation imaging apparatus according to claim 10, wherein the correction unit corrects only the first radiation image data based on the first offset data, and corrects the other radiation image data including the second radiation image data based on the offset data derived after deriving the other radiation image data.

13. A radiation imaging system comprising:

a radiation imaging apparatus according to claim 8; and
a radiation generator for generating radiation,
wherein the control unit switches a period of the radiation generated by the radiation generator.

14. The radiation imaging apparatus according to claim 8, wherein each of the plurality of pixels comprises conversion element for converting a radiation into an electric charge and switching element for outputting the electric signal according to the electric charge, the waiting operation in the first and second operation is an operation which the switching elements of the plurality of the pixels of the area sensor are turned off, and the read-out operation in the first and second operation is an operation which the switching elements of the plurality of the pixels of the area sensor output the electric signal line by line.

15. A method of controlling a radiation imaging apparatus comprising an area sensor for reading out an electric signal accumulated in a plurality of pixels arranged in a matrix, line by line, wherein the area sensor operates in a first operation for deriving radiation image data by reading a signal accumulated during an irradiation with radiation, and a second operation for deriving offset data by reading a signal accumulated during non-irradiation with the radiation, alternately, and wherein a frame rate is an inverse number of a sum of a first time for the first operation and a time for the second operation, and each of the first and second operations includes a waiting operation for accumulating the electric signal in the plurality of pixels of the area sensor and a read-out operation for reading out the electric signal accumulated in the plurality of pixels of the area sensor, comprising a step of:

controlling the area sensor, to switch the frame rate after an end of the read-out operation in the first operation and before the end of the read-out operation in the second operation which is continuous to the end of the read-out operation in the first operation, when switching of the frame rate is instructed.

16. The method according to claim 15, further comprising a step of:

correcting the radiation image data so that the radiation image data is not corrected based on the offset data which is acquired during switching of the frame rate, said offset data being data derived by the second operation operated during the time period from the end of the read-out operation in the first operation until the end of the read-out operation in the second operation.

17. The method according to claim 16, wherein, in the correction step, first radiation image is corrected based on first offset data, and second radiation image data is corrected based on second offset data, the first radiation image data being radiation image data derived immediately before switching of the frame rate, the first offset data being offset data derived before deriving of the first radiation image data, the second radiation image data being radiation image data derived immediately after switching of the frame rate, and the second offset data being offset data derived after deriving of the second radiation image data.

18. The method according to claim 17, wherein, in the correction step, only the second radiation image data is corrected based on the second offset data, and the other radiation image data including the first radiation image data is corrected based on the offset data derived before deriving the other radiation image data.

19. The method according to claim 17, wherein, in the correction step, only the first radiation image data is corrected based on the first offset data, and the other radiation image data including the second radiation image data is corrected based on the offset data derived after deriving the other radiation image data.

20. A method of controlling a radiation imaging apparatus comprising an area sensor for reading out an electric signal accumulated in a plurality of pixels arranged in a matrix, line by line, to derive two-dimensional data, wherein the area sensor operates in a first operation for deriving radiation image data by reading a signal accumulated during an irradiation with radiation, and a second operation for deriving offset data by reading a signal accumulated during non-irradiation with the radiation, alternately, and wherein the second operation is continuous to an end of the reading in the first operation, and a frame rate is an inverse number of a sum of a first time for the first operation and a second time for the second operation, and each of the first and second operations has a waiting operation for accumulating the electric signal in the plurality of pixels of the area sensor and a read-out operation for reading out the electric signal accumulated in the plurality of pixels of the area sensor, comprising a step of:

controlling the area sensor to switch the frame rate, from a first period of the first operation into a second period different from the first period, during a time period of the waiting operation and the read-out operation in the second operation which is continuous to the end of the read-out operation in the first operation.

21. The method according to claim 20, further comprising a step of:

correcting the radiation image data so that the correction unit does not correct the radiation image data based on the offset data which is acquired during switching of the frame rate, the offset data being data derived by the second operation operated during the time period the control unit switches the frame rate.

22. The method according to claim 20, wherein, in the correction step, first radiation image data is corrected based on first offset data, and second radiation image data is corrected based on second offset data, the first radiation image data being radiation image data derived immediately before switching of the frame rate, the first offset data being offset data derived before deriving of the first radiation image data, the second radiation image data being radiation image data derived immediately after switching of the frame rate, and the second offset data being offset data derived after deriving of the second radiation image data.

23. The method according to claim 22, wherein, in the correction step, only the second radiation image data is corrected based on the second offset data, and the other radiation image data including the first radiation image data is corrected based on the offset data derived before deriving the other radiation image data.

24. The method according to claim 22, wherein, in the correction step, only the first radiation image data is corrected based on the first offset data, and the other radiation image data including the second radiation image data is corrected based on the offset data derived after deriving the other radiation image data.

* * * * *